United States Patent
Pelissier

(10) Patent No.: US 6,325,759 B1
(45) Date of Patent: Dec. 4, 2001

(54) ULTRASOUND IMAGING SYSTEM

(75) Inventor: Laurent Pelissier, Vancouver (CA)

(73) Assignee: Ultrasonix Medical Corporation, Vancouver (CA)

( * ) Notice: Subject to any disclaimer, the term of this patent is extended or adjusted under 35 U.S.C. 154(b) by 0 days.

(21) Appl. No.: 09/401,923

(22) Filed: Sep. 23, 1999

(51) Int. Cl.[7] ................................................ A61B 8/00
(52) U.S. Cl. .................................................. 600/443
(58) Field of Search ..................... 600/437, 440–441, 600/443, 447; 128/916; 367/7, 11, 103–105; 73/625–626

(56) References Cited

U.S. PATENT DOCUMENTS

| | | | |
|---|---|---|---|
| 5,581,517 | * 12/1996 | Gee et al. | 367/138 |
| 5,709,209 | 1/1998 | Friemel et al. | |
| 5,758,649 | 6/1998 | Iwashita et al. | |
| 5,795,297 | 8/1998 | Daigle | |
| 5,839,442 | 11/1998 | Chiang et al. | |
| 5,853,367 | * 12/1998 | Chalek et al. | 600/437 |
| 6,126,601 | * 10/2000 | Gilling | 600/440 |

FOREIGN PATENT DOCUMENTS

WO 98/28631    7/1998   (WO).

OTHER PUBLICATIONS

Alfke, Peter. *XILINX,* Application Note (XAPP 052), Jul. 7, 1996, pp. 1–3.

* cited by examiner

*Primary Examiner*—Francis J. Jaworski
(74) *Attorney, Agent, or Firm*—Akin, Gump, Strauss, Hauer & Feld, L.L.P.

(57) ABSTRACT

An ultrasound imaging system includes a transducer, an ultrasound module, and a computer. The ultrasound module provides signal pre-processing and is highly programmable. The ultrasound module has several independently programmable functional units. The computer performs real-time scan conversion, display, data collection, user interface and input and output data exchange. The operational mode of the ultrasound module can be set under software control from the computer. The ultrasound imaging system is versatile, software-unreadable, and can perform a wide range of imaging applications in real-time. Several ultrasound imaging systems can be integrated as clients in a network of ultrasound devices having a client/server architecture for archiving, reporting and remote-control purposes.

19 Claims, 19 Drawing Sheets

ULTRASOUND IMAGING SYSTEM

FIELD OF THE INVENTION

This invention relates to ultrasound diagnostic imaging systems. In particular, this invention relates to an ultrasound diagnostic imaging system which includes a programmable digital ultrasound module and a software-controlled computer.

BACKGROUND OF THE INVENTION

Ultrasound imaging systems are used in medicine to explore internal areas of a patient's body. Ultrasonic imaging is non-destructive and versatile and can provide high quality diagnostic images.

A typical medical ultrasound imaging system has a transducer, a custom built electronic controller, and a user interface. The transducer typically has several piezoelectric transducer elements regularly placed on a frame. The transducer may have elements arranged in any of several different geometries, depending upon the medical application for which the transducer will be used. The controller drives the transducer and collects and processes data from the transducer to provide, store, display and manipulate images. The user interface may include various input/output devices which allow a user to control the operation of the imaging system. The input/output devices typically comprise at least a control panel, a video display, and a printer.

The electronic controller can send and receive electric signals to and from any of the transducer elements. To create a diagnostic image, the controller transmits electrical excitation signals to the transducer elements. The transducer elements convert the excitation signals into ultrasonic vibrations which are transmitted into the patient's body. The ultrasonic vibrations typically have frequencies in the range of about 2 MHz to about 12 MHz. The ultrasonic vibrations are scattered and reflected by various structures in the patient's body. Some of the reflected and/or scattered ultrasonic vibrations, which may be called echoes, are received at the transducer. The echoes cause the transducer elements to generate electrical signals. After the excitation signals have been transmitted the controller receives and processes the electric signals from the transducer elements.

The resulting image is displayed in real time on a display. The classic presentation of the display, called B-mode, is a two-dimensional image of a selected cross-section of the patient's body. It is desirable to obtain high resolution images and so state of the art medical ultrasound imaging system provide dynamic digital focusing and adaptive filtering systems which process the signals received from numerous transducer elements. Another commonly used presentation, called M-mode, shows a particular line of the image, displayed as a function of time on the screen. M-mode images are useful for displaying temporal information.

To provide more diagnostic information, ultrasound imaging systems typically include digital signal-processors which process the echoes to determine blood flow velocity at points in the patient's body. The blood flow velocity can be measured by using Doppler processing techniques to extract the Doppler signal. The Doppler signal can then be processed by Fast Fourier Transform (FAT) techniques. The color of individual pixels in an image may be set to a value which indicates blood velocity at that point. A Doppler signal can also be extracted, processed by using auto correlation techniques to extract blood speed average and variance information in each point of a region of interest.

Commercially available medical ultrasound units typically have many custom made electronic boards which each perform specific tasks and which are hard wired together to provide desired imaging modes. This architecture has been considered necessary to achieve high quality ultrasound signal processing and display in real-time. Manufacturing, upgrading and maintaining such systems is undesirably expensive. Since these systems use their own standards, it is also more expensive to develop user software, and more expensive than desirable for customers to acquire network and archiving systems compatible with the ultrasound imaging system.

U.S. Pat. No. 5,758,649 to Iwashita et al. describes a system for generating ultrasound images. The system includes a module which performs analog beam-forming, preprocessing, scan image conversion and display. This module is designed to be used in conjunction with a computer. The module can be interfaced to a networked general purpose computer system. Images generated by the module can be displayed on the computer. The ultrasound imaging system described in Iwashita et al. uses hard wired electronic boards for preprocessing, scan conversion, and postprocessing.

U.S. Pat. No. 5,839,442 to Chiang et al. describes a portable ultrasound imaging system comprising a computer and a miniaturized analog beam-former integrated in a transducer. This system also uses application-specific hard wired electronic boards to perform signal preprocessing. The scan conversion and display software described provides only restricted post-processing.

U.S. Pat. No. 5,795,297 to Daigle describes an ultrasound imaging system comprising a beam-former and a personal computer. The computer is responsible for almost all processing except beam-forming. The Daigle system is not capable of performing in real time many of the more sophisticated tasks which are now expected of diagnostic ultrasound systems. For a typical digital ultrasound real-time imaging system, implementing a 128 channel digital beam-former needs about 500,000 MIPs (million instructions per second), an echo-level preprocessor needs about 600 MIPs, a color Doppler preprocessor needs about 2,000 to 5,000 MIPs and a scan converter needs about 150 MIPs. Currently available personal computers and workstations can typically handle 200 to 1,000 MIPs with added digital signal-processing boards. This is sufficient to perform scan conversion in real-time. However, echo-level preprocessing with color Doppler preprocessing cannot be performed in real-time on such platforms. Furthermore, presently available real-time operating systems for personal computers are capable of interrupting in a minimum of 2 milliseconds. This makes it necessary to have a hardware controller for the transmit and receive sequencing.

There remains a need for a flexible, versatile and programmable ultrasound imaging system. There is a particular need for such systems which are based on readily available computers but which can provide sophisticated digital real-time imaging.

SUMMARY

This invention relates to an ultrasound imaging system including an ultrasound module, and a computer. A transducer converts electric signals into acoustic signals, and acoustic echo signals into electrical echo signals. The ultrasound module generates electrical transmit signals and receives the electrical echo signals, and produces pre-processed data from the echo signals. The computer programs the ultrasound module, and performs post-processing and display processing for producing an ultrasound diagnostic image. The computer also stores ultrasound images and handles input/output devices interfacing and networking.

The imaging system of the invention is highly configurable. A preferred embodiment of the invention provides an ultrasound imaging system comprising a signal pre-processing module. The signal pre-processing module has an input for receiving echo signals from an ultrasound transducer; a signal path extending from the input to an output. A programmed computer receives data from the output. The computer further processes the pre-processed data to yield an ultrasound image. The imaging system includes at least one software configurable signal processing circuit in the signal path. This permits the imaging system of the invention to process data in many different ways to provide various operational modes without the need to remove and replace hardware. A configuration bus connects the computer and the signal pre-processing module. Software running on the computer is adapted to configure the software configurable signal processing circuit by sending configuration data over the configuration bus. In preferred embodiments of the invention the software comprises a user interface which allows a user to select from among several alternative operational modes. After an operational mode has been selected the software selects configuration data appropriate to the selected operational mode and sends the configuration data to the signal pre-processing module on the configuration bus.

Further features and advantages of the invention are described below.

BRIEF DESCRIPTION OF THE DRAWINGS

Drawings which illustrate non-limiting embodiments of the invention are appended in which.

DETAILED DESCRIPTION

Overview

This invention provides an ultrasound imaging system which has a number of "programmable blocks" which can be configured under software control to place the imaging system in different operational modes. Operating parameters which govern the behavior of the imaging system within each operational mode can also be set under software control. The architecture of ultrasound imaging systems according to the invention can be used to provide multi-application, programmable and versatile ultrasound imaging systems capable of supporting all usual imaging modes in real-time. Because each programmable block is individually software controllable the imaging system can be upgraded in various ways by simply changing software. For example, new real-time imaging algorithms, new focusing methods as well as new calculations, or new networking protocols can often be implemented without changing hardware in a system according to the invention.

A standard general purpose computer may be used to control an imaging system according to the invention. This facilitates software development. Instead of developing software to run on custom specialized hardware, a programmer can take advantage of existing tools and libraries for the operating system of the general purpose computer to build a friendly and familiar user interface, handle input/output devices and network protocols. Further, a system according to the invention may use fewer custom circuit boards than a conventional diagnostic ultrasound system as certain functions are handled in software. This further reduces the cost of manufacturing, maintaining and upgrading an ultrasonic imaging system.

Figure 1:
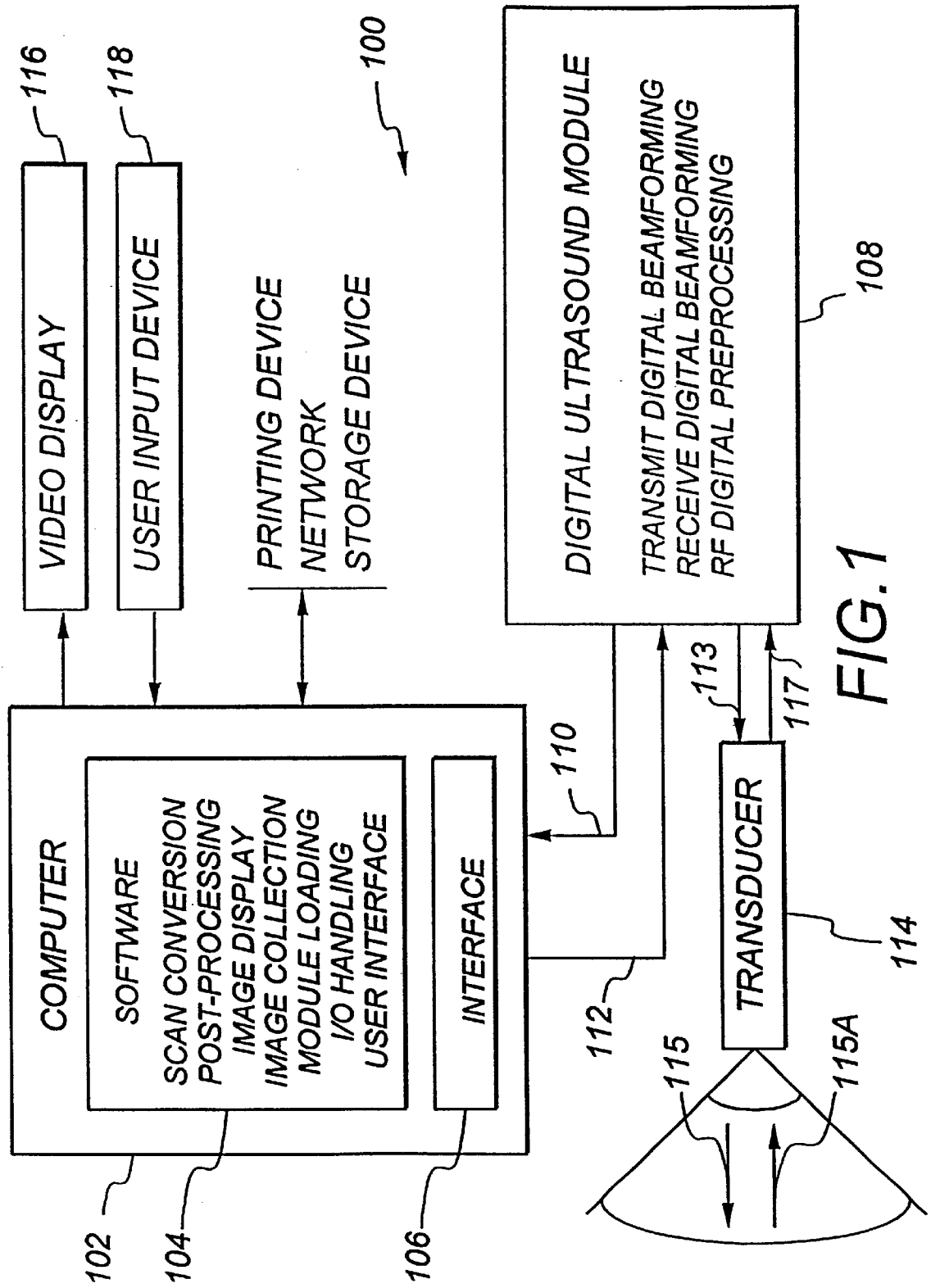
FIG. 1 is an ultrasound system for producing ultrasound images according to a first embodiment of the invention.

FIG. 1 is a block diagram of an ultrasound imaging system 100 for producing ultrasound images. System 100 is an example embodiment of the invention. The invention is not limited to the specific features of system 100. System 100 includes an ultrasound module 108 and a computer 102. Module 108 is coupled to a transducer 114. Module 108 generates driving signals 113 which are directed to transducer 114. Transducer 114 generates acoustic signals 115 in response to driving signals 113. Acoustic signals 115 are directed into an object to be imaged, such as the body of a patient.

Some parts of acoustic signals 115 are reflected back to the transducer 114 as echo signals 115A. The elements of transducer 114 receive echo signals 115A and, in response create electrical echo signals 117. Ultrasonic imaging involves deriving information about structures within the object being imaged from echo signals 117. Echo signals 117 are directed to module 108 for pre-processing. Data pre-processed by module 108 is received at computer 102 where it is further processed and displayed.

An elementary 1-dimensional ultrasound image, called a rayline, may be generated by transmitting acoustic signals 115 in a desired direction, receiving echo vibrations 115A, converting echo vibrations 115A into echo signals 117, and pre-processing echo signals 117. 2-dimensional or 3-dimensional ultrasound images may be assembled from a number of 1-dimensional ultrasound images. Typical ultrasound images are composed of a plurality of raylines. A 2-dimensional ultrasound image, such as a B-mode image, may be generated from a plurality of raylines each passing through a different portion of the object being imaged. To generate a 2-D ultrasound image module 108 is configured to sequentially image each of the required raylines. An M-mode image may be created by periodically taking sequential images along the same rayline.

Module 108 can be configured to operate in various different operational modes under the control of software 104. In each operational mode, module 108 may provide a different form of driving signals 113 and/or process echo signals 117 in a different manner. The operational mode determines the gross behavior of system 100. In each operational mode system 100 typically assembles an image from a number of raylines. The precise way in which acoustic signals 115 are generated and echo signals 117 are processed to yield pre-processed data 110 is specified by a set of rayline parameters which are provided by software 104. The rayline parameters may be different for each rayline. Different sets of rayline parameters may be used in each operational mode of system 100. Rayline parameters typically include base addresses for various memories in which data or software is stored, rayline-specific filter coefficients, control codes which specify, for example, whether or not a transmitting sequence is to be repeated, and so on.

Module 108 has an input at which echo signals 117 are received. Module 108 pre-processes echo signals 117. Pre-processing generates a set of data vectors which are available at an output of module 108. The pre-processed data vectors may be referred to as pre-processed data 110. Pre-processed data 110 is sent to computer 102 via an interface 106. The pre-processing provided by module 108 reduces the computational effort needed to create images from pre-processed data 110 sufficiently that computer 102 is capable of generating ultrasound diagnostic images in real-time from pre-processed data 110. Computer 102 displays the ultrasound diagnostic image on a video display 116 connected to computer 102.

The display processing performed by computer 102 preferably includes a display and scan conversion algorithm that can be executed in real-time by software 104 on computer 102. Software 104 preferably provides various post-processing features such as image persistence or gamma correction. Software 104 also provides a graphic user interface which enables users to configure system 100, edit patient information and fine tune the operation of system 100. User input is received from one or more user input devices 118. User input devices may include keyboards, pointing devices, voice recognition systems, touch screens or the like.

Module Operation

Figure 3:
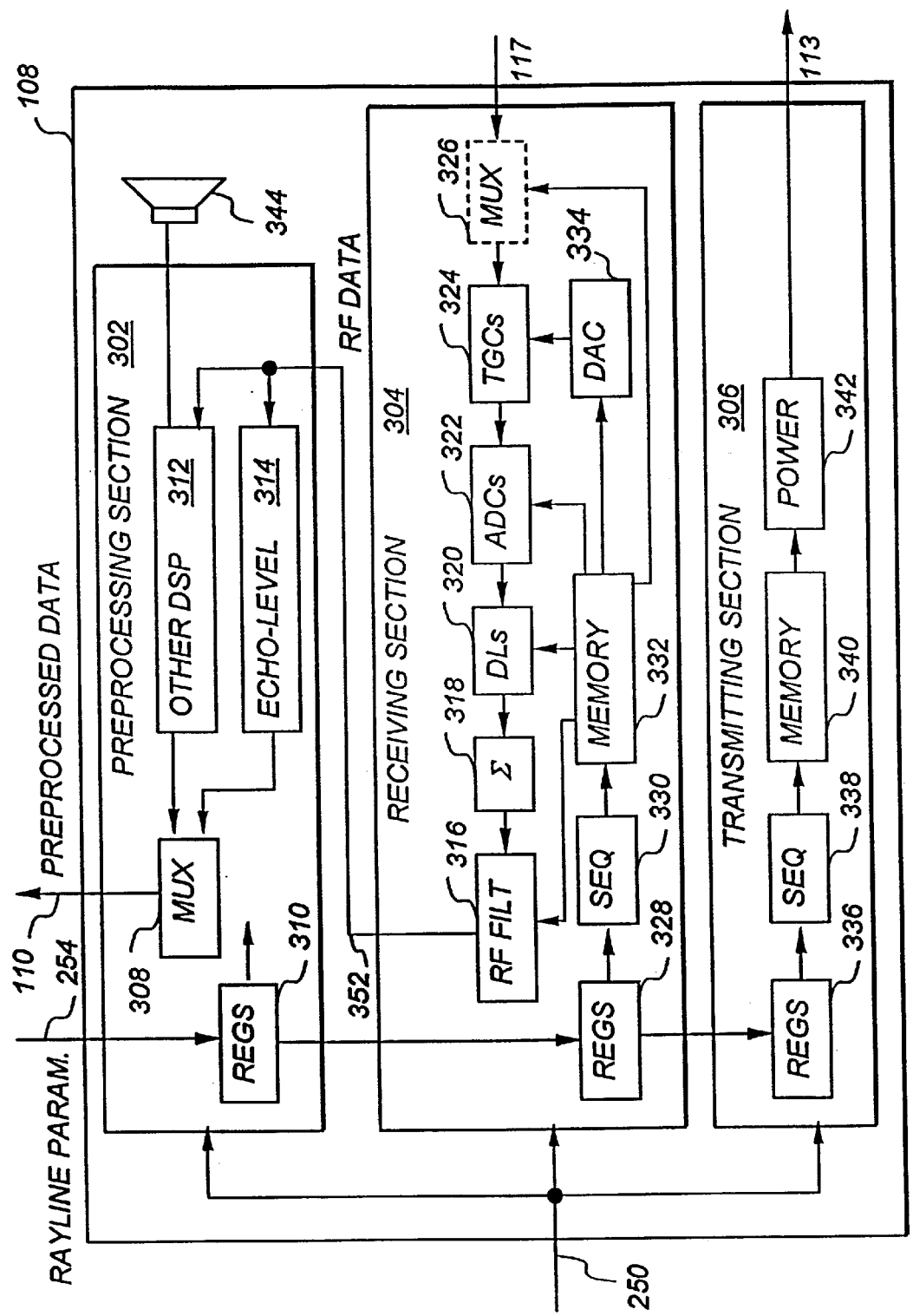
FIG. 3 is a block diagram of an ultrasound module, according to an embodiment of the invention.

FIG. 3 is a block diagram of a module 108 according to a preferred embodiment of the invention. Module 108 has a transmitting section 306, a receiving section 304 and a preprocessing section 302. It can be convenient to make each of sections 302, 304, and 306 on a separate circuit board.

Transmitting section 306 has a serial to parallel registers block 336, a transmitting sequencer 338, a transmitting memory 340 and a power interface 342. Transmitting section 306 can be configured to provide different driving signals 113 for the creation of different types of images. The form of driving signals 113 delivered to the elements of transducer 114 governs the waveform and direction of propagation of vibrations 115. As is known in the art, the vibrations 115 generated by transducer 114 can be focused and steered by varying the relative phases of signals 113 used to drive the different elements of transducer 114.

When a user selects an operational mode for system 100 software 104 loads memory 340 with data specifying appropriate waveforms for the driving signal 113 to be applied to each element of transducer 114. If the operational mode requires multiple raylines then memory 340 may contain different waveforms for each rayline. Memory 340 preferably contains a sequence of bits for each element. Each bit specifies whether the corresponding element of the transducer is "on" or "off" during a given period after the start of a rayline. System 100 can accommodate transducers 114 of various configurations or cause raylines to be taken in a different set of directions simply by writing different data to memory 340.

Figure 5C:
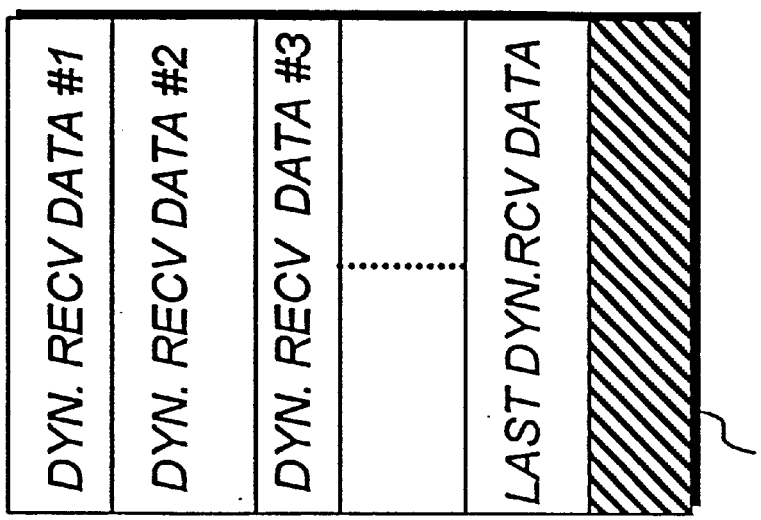
FIG. 5 is an illustration of the memories arrangement, according to an embodiment of the invention.
Figure 5B:
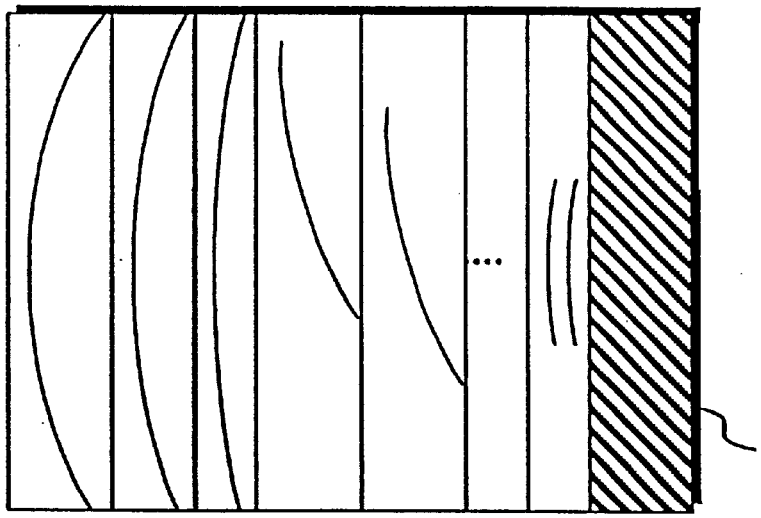

Memory 340 is at least wide enough to specify driving signals 113 for each element of transducer 114. Transmitting memory 340 is at least M bits wide, M being the number of elements of the transducer 114. In typical transducers M is 128 or more. FIG. 5B represents the M bits horizontally, and the addresses vertically.

Data from memory 340 is retrieved and sent to power interface 342 by a sequencer 338. At the start of a transmitting sequence, sequencer 338 retrieves a row of bits from memory 340 starting at a base address and forwards those bits to power interface 342. Sequencer 338 periodically (typically every 200 microseconds) retrieves a succession of rows of bits (typically at 40 Mhz) from memory 340 and forwards those bits to power interface 342. The base address may be specified by the rayline transmitting parameters.

Power interface 342 comprises a series of switches controlled by the bits output by sequencer 338, and a high voltage supply. Each switch causes a corresponding element in transducer 114 to be "on" or "off" depending upon the value of the corresponding bit received from memory 340. The signals 113 output by power interface 342 are sent to transducer 114 through appropriate adaptation circuitry (not shown).

For each rayline, software 104 causes interface 106 to send appropriate rayline parameters to registers 336. Rayline parameters applicable to transmitting section 306 or "rayline transmitting parameters" for the current rayline are available at the outputs of registers 336. The rayline transmitting parameters include a base address to use in memory 340, a number which specifies the interval after which to retrieve a succession of rows of bits from a next address in memory 340, a number which represents the length of the transmitting sequence and optionally a number of clock cycles after which sequencer 338 recycles to the base address. Sequencer 338 uses the rayline transmitting parameters in registers 336 to address memory 340. Depending on the rayline transmitting parameters, the transmitting can be repetitive or not. The transmitting sequences may have different sizes for different raylines. Memory 340 may store a number of different transmitting sequences which each begin at a different base address. Software 104 can cause system 100 to switch to a different transmitting sequence by specifying a set of rayline parameters which include a different base address in memory 340.

After a signal is transmitted by transducer 114, echo signals 117 received by each element of transducer 114 are sent to receiving section 304 through appropriate adaptation circuitry (not shown). Module 108 processes echo signals 117 by passing signals 117 along a signal path extending between the input of module 108 and interface 106. The signal path passes through receiving section 304 and pre-processing section 302. Along the signal path, echo signals 117 from each element of transducer 114 are processed. Processing typically includes converting signals 117 into digital values, beam-forming, summing, filtering and further processing signals 117 to generate pre-processed data 110. Pre-processed data 110 may represent echo amplitude information, velocity information and/or other information useful for diagnostic purposes. How echo signals 117 are processed to yield pre-processed data 110 depends upon the operational mode of module 108.

Separate transducer elements could be used for transmitting signals 115 and for receiving echoes 115A. The transducer 114 which receives echoes 115A has M elements. Receiving section 304 can handle N channels. Receiving section 304 has a group of N TGC (Time Gain Control) amplifiers 324, a group of N Analog to Digital Converters ("ADCs") 322, a group of N digital delay lines 320, a digital summing circuit 318, and a RF digital filtering circuit 316 in the signal path. Receiving section 304 also has a register block 328, a receiving sequencer 330 and a memory block 332 which are used to receive rayline parameters from interface 106. Software 104 configures interface 106 to send appropriate rayline parameters for the current operational mode of system 100. The rayline parameters control the operation of receiving section 304 within the constraints imposed by the operational mode of module 108. FIG. 5C shows the arrangement of data in receiving memory block 332.

Receiving memory block 332 can hold control values for TGC amplification, focusing, and RF filtering. Memory 332 is wide enough to provide all these values for N channels. Sequencer 330 initially addresses a base address in memory 332. The values stored at the base address are provided to RF filter 316, Delay lines 320, ADCs 322 and TGCs 324. During the collection of data for a rayline, sequencer 330 periodically addresses a next address in memory 332. Sequencer 330 may address a new address in memory 332 every 1 microseconds. This allows dynamic adjustment of the amplification, focusing, and filtering. The number of values needed for each rayline varies. Receiving memory block 332 can hold values which provide for adjustment of TGC amplification, dynamic focusing and dynamic RF filtering over wide ranges. That allows dynamic multiple angular focusing, rayline-adapted TGC amplification and RF filtering. Different operating modes of module 108 may use different base addresses within memory 332.

Multiplexers 326 are preferably provided for use in case the number of channels N is smaller than the number of elements M in transducer 114. Each rayline may use information from different ones of the M elements of transducer 114. The selection of the group of multiplexers 326 may be specific to each rayline and specified by the rayline parameters.

The N echo signals 317 are forwarded to N TGC amplifiers 324. TGC amplifiers 324 are controlled by a voltage, generated by a Digital to Analog Converter ("DAC") 334. ADCs 322 convert the N amplified echo signals to N digital values. The analog to digital sampling frequency is set by a clock generator 220 on interface board 214. A clock signal from clock 220 is provided to module 108 via, for example, configuration bus 250 or trigger signals bus 252.

The outputs of ADCs 322 are forwarded to delay lines 320. Delay lines 320 are preferably digital delay lines which may be implemented as register lines in Field Programmable Gate Arrays ("FPGAs") or Application Specific Integrated Circuits ("ASICs"). Each delay line 320 delays a digital input signal by a predetermined amount. The relative delay between different delay lines 320 can be increased or decreased by enabling or disabling the clock signal which causes data values to propagate along one of delay lines 320. FPGAs containing dual port fast memory may be used to implement delay lines 320. Delay lines 320 may, for example, be implemented using Xilinx™ XC4000E FPGAs available from Xilinx, Inc. of San Jose Calif. as described in Xilinx application note No. XAPP 052.

Summing circuit 318 sums the N digital values available at the outputs of delay lines 320. The resulting stream of beam-formed echo signal digital values is sent to filter 316. Summing circuit 318 and delay lines 320 provide a dynamically software-configurable digital beam-former. This beam former can accommodate multiple angular focus, repetitive shots, and changes in transducer frequency.

Filter 316 is a multi-tap digital filter. Summer 318 and filter 316 may be implemented as a group of multiplier and summer circuits in a FPGA (Field Programmable Gate Array). The overall configuration of summer 318 and filter 316 are determined by the operational mode of module 108. Different operational modes may implement completely different summing and filtering algorithms or may replace summing and filtering with other processing stages. Filtering tap coefficients may be specified as part of the rayline parameters applicable to receiving section 304 "rayline receiving parameters" which may be loaded dynamically as described below.

In some or all operational modes, the architecture of summer 318 and filter 316 may be pipelined to enable high frequency capabilities. Pipelining involves dividing the global architecture into several blocks, separated by registers. The output is time delayed since it is registered several times, but the sampling clock frequency can be high. For example, an 8-tap digital filter may be implemented as 8 multipliers followed by 8 registers, followed by 4 adders (each of which sum the values in a pair of the 8 registers) followed by 4 registers, followed by 2 adders (each of which sum the values in a pair of the 4 registers), followed by 2 registers, followed by one adder which adds the values in the two registers. It takes 3 clock cycles to generate an output of the filter. However, a new data point can be accepted every clock cycle. The digitized, beam-formed, and filtered, RF echo signal output from filter 316 may be called "RF data". RF data is sent to pre-processing section 302 on a RF data bus 352.

Rayline receiving parameters are available at the output of register 328. The rayline receiving parameters include a base address in memory 332. When pre-processing of signals 317 for a rayline begins, sequencer 330 addresses a block in memory 332 at the base address. The data values in the memory block are provided to the components of receiving section 304. Periodically (for example, every 1 microsecond) sequencer 330 shifts to address a next memory block in memory 332, thereby providing a new set of data values to the different components of receiving section 304. This permits dynamic adjusting of the TGC amplification, beam-forming delays, and RF filtering coefficients.

Pre-processing section 302 receives the RF data, pre-processes the RF data and outputs pre-processed data 110. Pre-processing section 302 comprises an echo-level preprocessing unit 314, a digital signal-preprocessing unit 312 and an output multiplexer 308 in the signal path. Pre-processing section 302 also comprises a register block 310 for use in providing rayline parameters applicable to pre-processing section 302 "rayline pre-processing parameters".

Echo-level pre-processing unit 314 receives the RF data on RF data bus 352. Echo-level pre-processing unit 314 performs an echo-level detection with adaptive filtering, on the RF data. The output of the echo-level pre-processing unit 314 is a detected echo level for a number of discrete points along a rayline. The echo levels can be displayed to provide an echo-level diagnostic image. The detected echo levels are output from pre-processing unit 314 at a lower rate than the sampling frequency of ADCs 322. The rate at which echo levels are generated is low enough that computer 102 can use the detected echo levels for real-time post-processing and display. The ratio of the data rate at the input of echo-level preprocessing unit 314 to the data rate at the output of echo-level preprocessing unit 312 might be about 8:1 for example.

Signal pre-processing unit 312 operates in parallel with echo-level pre-processing unit 314 and performs specific additional data vector estimation. If signal pre-processing unit is sufficiently powerful then it may provide both echo-level detection and additional pre-processing in which case a separate echo-level pre-processing unit is not required. Signal pre-processing unit 312 performs a set of computations which can be specified by computer 102 under the control of software 104 during the selection of the operational mode of module 108. For example, signal pre-processing unit 312 may perform calculations which provide velocity estimation for CFM (Color Flow Mapping) imaging, Power imaging, Pulsed Wave Doppler imaging or Continuous Wave Doppler imaging. Signal pre-processing unit 312 receives the RF data, performs calculations on the RF data and outputs pre-processed data at a rate lower than the data rate of the RF data. The ratio of the data rate at the input of preprocessing unit 312 to the data rate at the output of preprocessing unit 312 might be about 16:1 for example. If needed, signal-preprocessing unit 312 can directly output audio signals to speakers 344. This feature might be used to audibly reproduce a Doppler signal, for example.

The configuration of each of signal pre-processing unit 312 and echo-level preprocessing unit 314 are specified by software 104 when the operational mode of module 108 is selected. The behavior of signal pre-processing unit 312 and echo-level pre-processing unit 314 can be modified according to rayline pre-processing parameters, which are available at the output of registers 310. Registers 310 may be implemented in a FPGA so that their configuration can be set up by software 104. The rayline pre-processing parameters include echo-level preprocessing parameters which specify configurations for the echo-level pre-processing unit 314, and signal-processing parameters sent to the signal pre-processing unit 312. This facilitates configuring pre-processing section 302 to provide appropriate pre-processing for each rayline. The rayline preprocessing parameters further include selection parameters sent to the selection lines of output multiplexer 308. The selection parameters determine whether the output from unit 312 or the output from unit 314 is delivered to computer 102 as preprocessed data 110.

Figure 4A:
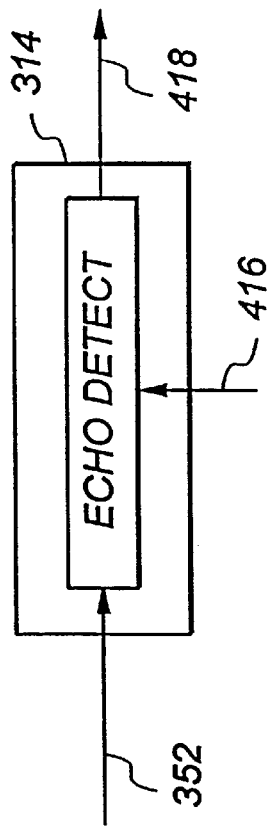
FIG. 4 is a detailed block diagram of a preprocessing system, according to an embodiment of the invention.

FIG. 4A is a detailed block diagram of echo-level pre-processing unit 314. Echo-level pre-processing unit 314 may be implemented completely in a FPGA. Thus, echo-level pre-processing unit 314 can be fully configurable dynamically. FPGA 418 is configured to provide circuitry which performs echo-level detection and filtering. The input data is the RF data on RF data bus 352. The rayline echo-level preprocessing parameters on bus 416 provide detection coefficients. The data output from echo-level pre-processing unit 314 is sent to output multiplexer 308 through a bus 418. Output multiplexer 308 is responsible for sending either the echo level generated by echo-level pre-processor 314 or the estimated data vector provided by signal pre-processing unit 312 to computer 102 as pre-processed data 110.

Figure 4B:
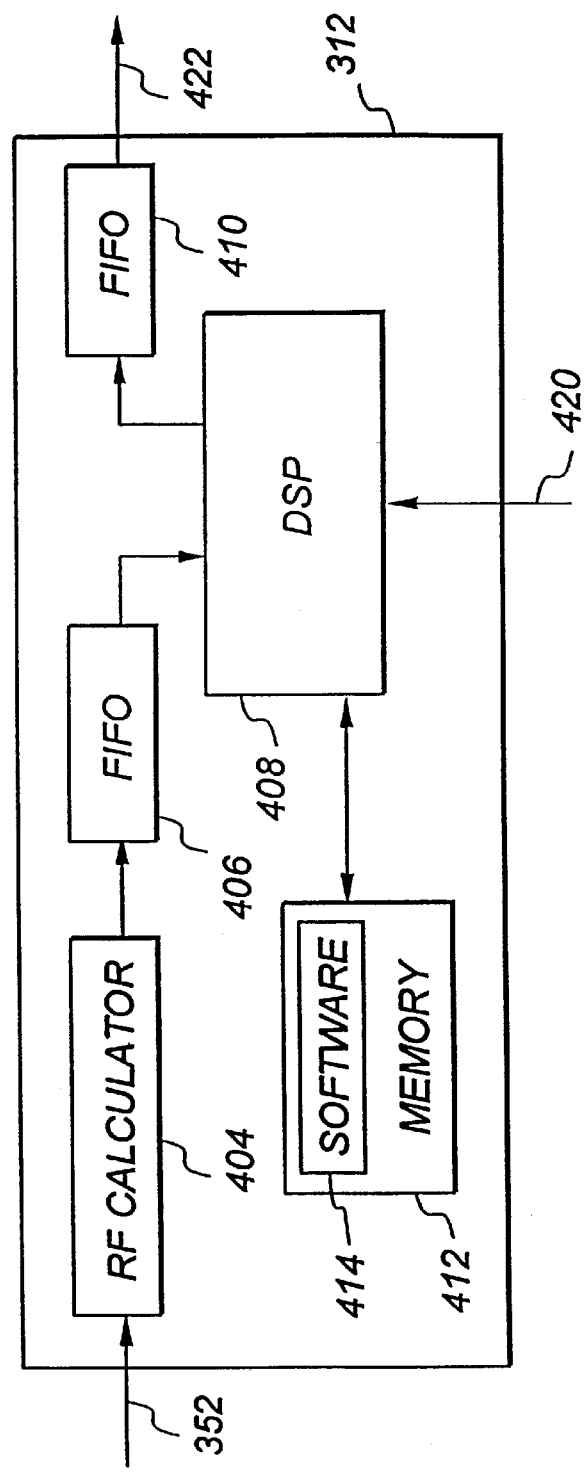

FIG. 4B is a detailed block diagram of digital signal-preprocessing unit 312. Signal-preprocessing unit 312 comprises a RF calculator 404, a pre-DSP FIFO 406, a DSP (Digital Signal Processor) 408, a post-DSP FIFO 410, and a memory 412. The RF data signal is received by RF calculator 404 on RF data bus 352. RF calculator 404 may be implemented in a FPGA. Thus, RF calculator 404 is fully configurable dynamically. RF calculator 404 performs the first RF computations in order to convert the RF data into DSP-formatted data. RF calculator 404 might typically be configured to perform a complex demodulation of the RF data or to simply store a sequence of RF data values. The DSP-formatted data, which is the result of the real-time computations made by the RF calculator 404, is output at a lower rate than the data rate of the RF data and thus can be read in real-time by the DSP 408. For example, the data rate of the RF data may be 40 Mhz and the data rate at the input of DSP 408 might be 5 Mhz. The output from DSP 408 is at a lower rate still. The output from signal-preprocessing unit 312 is sent to the output multiplexer 308 through a bus 422.

DSP-formatted data from the output of RF calculator 404, is written in the pre-DSP FIFO 406. DSP 408, which is controlled by DSP software 414, continuously reads the pre-DSP FIFO 406 to retrieve the DSP-formatted data. DSP 408 runs DSP software specified by software 104 to perform specific real-time digital signal-processing algorithms. For example, DSP software 414 may cause DSP 408 to perform filtering and auto correlation when system 100 is in color Doppler mode. When system 100 is in pulsed or continuous wave Doppler mode DSP software 414 may cause DSP 408 to perform a demodulation followed by a fast fourier transform ("FAT"). DSP software 414 preferably includes software for performing two or more different processing algorithms. For each rayline, the DSP software 414 may read a rayline parameter to determine which processing algorithm to use. The results of the computations performed by DSP 408 are written in the post-DSP FIFO 410. These results may be called "estimated data vectors".

Computer Interface

Figure 2:
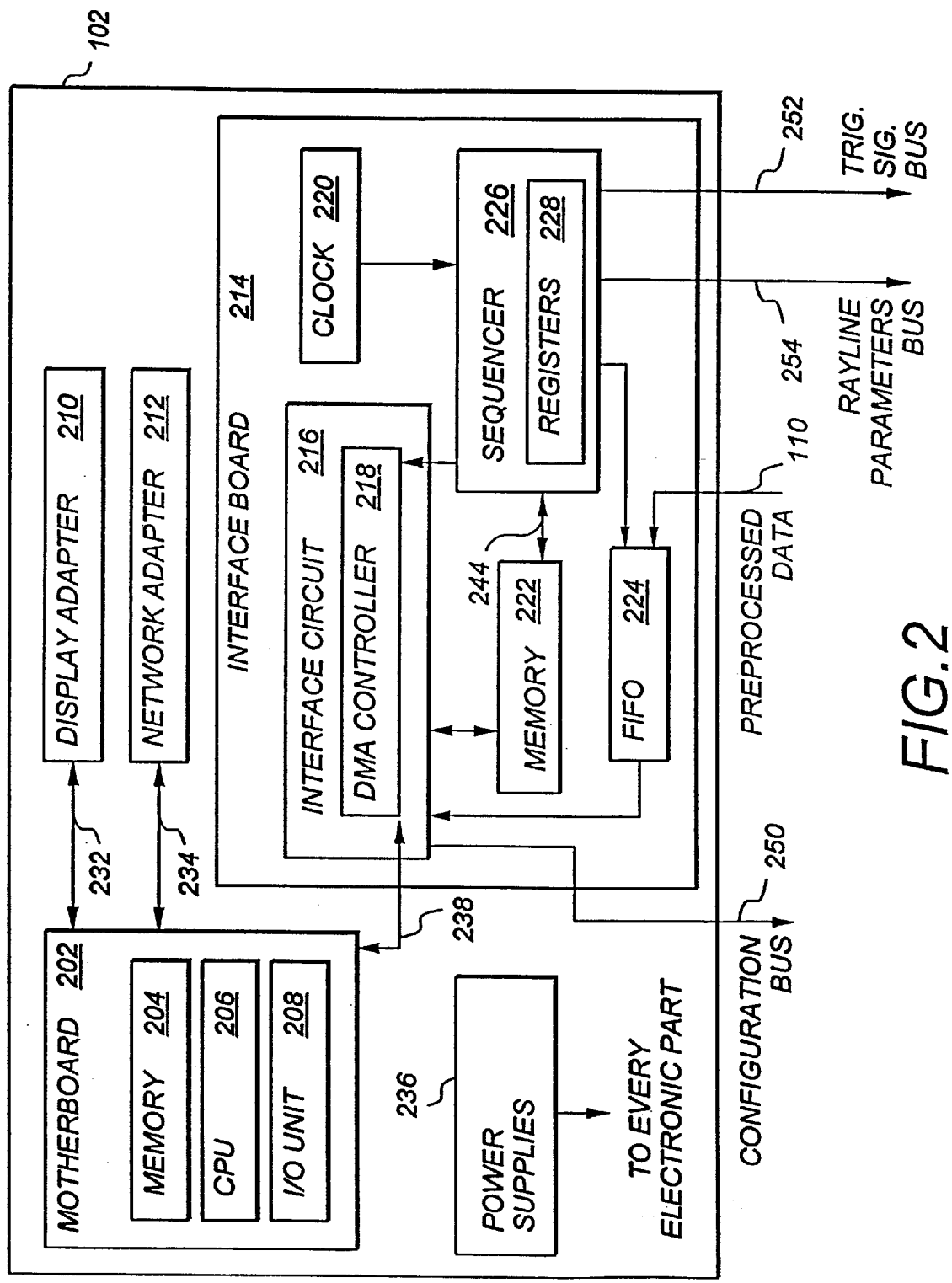
FIG. 2 is a block diagram of a computer, according to an embodiment of the invention.

FIG. 2 is a block diagram which illustrates computer 102. Computer 102 may be a standard personal computer equipped with an interface board 214 which includes interface 106. A typical computer 102 has a motherboard 202 which carries a CPU (Central Processing Unit) 206, memory 204 and I/O (input/output) circuitry 208. CPU 206 may be, for example, an Intel Pentium™ microprocessor or a Power PC™ microprocessor. Memory 204 may be a standard computer memory. I/O circuitry 208 interfaces with I/O ports such as USB (Ultra-fast Serial Bus) ports, serial ports, and/or parallel ports. I/O circuitry 208 may also provide an interface to an I/O bus such as a SCSI bus. Power for the various components of system 100 is provided by a power supply 236. A display adapter 210 is coupled to motherboard 202 through a suitable bus 232. Bus 232 may be, for example, an AGP (Advanced Graphic Port) bus. Display adapter 210 drives display device 116.

Interface board 214 is coupled to motherboard 202 through a bus 238. Bus 238 must be fast enough to handle data rates of at least twenty megabytes per second. Bus 238 may be, for example, a PCI bus. Buses 232 and 238 may be the same bus. Interface board 214 comprises a computer interface circuit 216, a clock generator 220, a rayline parameters memory 222, a FIFO (First In First Out buffer) 224 for receiving pre-processed data 110 from module 108 and a sequencer 226.

Interface 216 provides 2-way communication with module 108. When the operational mode of module 108 is being set, interface 216 transfers configuration data for one or more FPGAs in module 108 and software for any DSPs (or other processors) in module 108 to destinations in module 108. Configuration data 112 is sent from computer 102 to module 108 via bus 238, interface 216 and a configuration bus 250. Since bus 238, between the computer motherboard 202 and interface board 214, and configuration bus 250 are fast buses module 108 can be placed into a desired operational mode very quickly. Configuration bus 250 includes one or more lines that can be used as address lines so that each set of configuration data is directed to the correct destination in module 108.

Figure 5A:
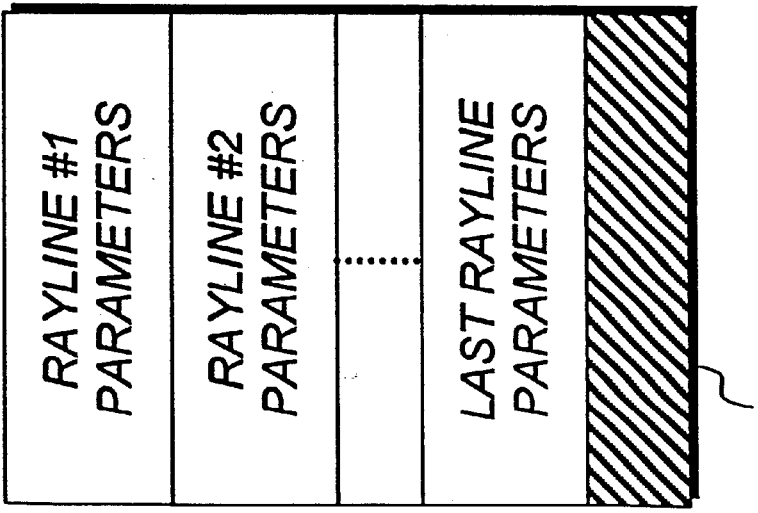

CPU 206 loads memory 222 with rayline parameters via interface circuit 216. The rayline parameters are data vectors which cause module 108 to operate appropriately to acquire and pre-process echo signals for each rayline in an image. FIG. 5A shows the rayline parameters in memory 222. Memory 222 contains successive groups of bytes, which contain the rayline parameters for successive raylines. For convenience, memory 222 may be eight bits wide.

After an operational mode has been selected and system 100 is operating, interface 216 transmits rayline parameters to module 108. The rayline parameters are propagated to different parts of module 108 by a serial to parallel registering architecture, as discussed below. Some rayline parameters may be used for sequencing. The sequencing rayline parameters may specify things such as the duration of each rayline, base memory addresses for loading programs or data, and so on. Other rayline parameters affect how computations are performed. A trigger signals bus 252 carries trigger signals to module 108. Trigger signals bus 252 carries a number of trigger signals including a clock signal from clock 220, a start new rayline signal, and a propagate rayline parameters signal which causes 1 byte of rayline parameters to be propagated from registers 228 into registers 310, 328 and 336. The "start new rayline" and "propagate rayline parameters" signals are generated by sequencer 226 as described below.

Pre-processed data 110, from ultrasound module 108, is received at and written in FIFO 224. Interface circuit 216 includes a DMA (Direct Memory Access) controller 218 which can master bus 238. DMA controller 218 continuously transfers pre-processed data 110 from FIFO 224 to a specified address in the computer memory 204 via bus 238. Thus, all of the pre-processed data for an image is assembled in a DMA destination block 804 in memory 204. To achieve this, software 104 programs DMA controller 218 to specify the destination in memory 204 for the pre-processed data 110 for each rayline (or for successive groups of raylines).

Since the OS of computer 102 and the bus controllers of interface 106 handle memory accesses, system 100 does not need dedicated special purpose memory for holding images in computer 102. To increase the cineloop capacity, the main memory of computer 102 could be replaced by a larger memory. A 32 megabyte memory block is sufficient to store approximately 128 ultrasound images with color, and about 8 minutes of M-mode, color M-mode or Wave Doppler mode.

DMA destination memory block 804 is a block of the computer memory 204, which has a size sufficient to contain pre-processed data 110 for the number of raylines used for display. For each DMA transfer, the destination address within the DMA destination memory block 804 can be given by the rayline parameters or by a table at a location in memory 204 accessible to DMA controller 218.

Propagation of Rayline Parameters

After module 108 has been configured for a desired operational mode sequencer 226 causes rayline parameters to be transmitted to module 108. Sequencer 226 reads memory 222, through bus 244 to retrieve the rayline parameters for the next rayline. The rayline parameters are loaded into serial to parallel registers 228 in sequencer 226. After the rayline parameters have been propagated into registers 228 they are transmitted to module 108 over rayline parameters bus 254. For each rayline in the desired image, rayline parameters, received from sequencer 226 on rayline parameters bus 254, are propagated onto pre-processing section 302, receiving section 304 and transmitting section 306.

In accordance with the rayline parameters, sequencer 226 generates trigger signals, which are forwarded to ultrasound module 108 on trigger signals bus 252. For example, some of the rayline parameters 228 may specify the duration of the current rayline and whether the current rayline is a last rayline in an image. During each rayline, sequencer 226 generates a signal to cause the rayline parameters for the next rayline to be propagated into registers 228, 310 328 and 336. Sequencer 226 uses a counter to specify the number of rayline parameter bytes to read for each rayline. After the last rayline in an image has been completed sequencer 226 generates a "$start_{13}$ $new_{13}$ rayline" signal.

Figure 6:
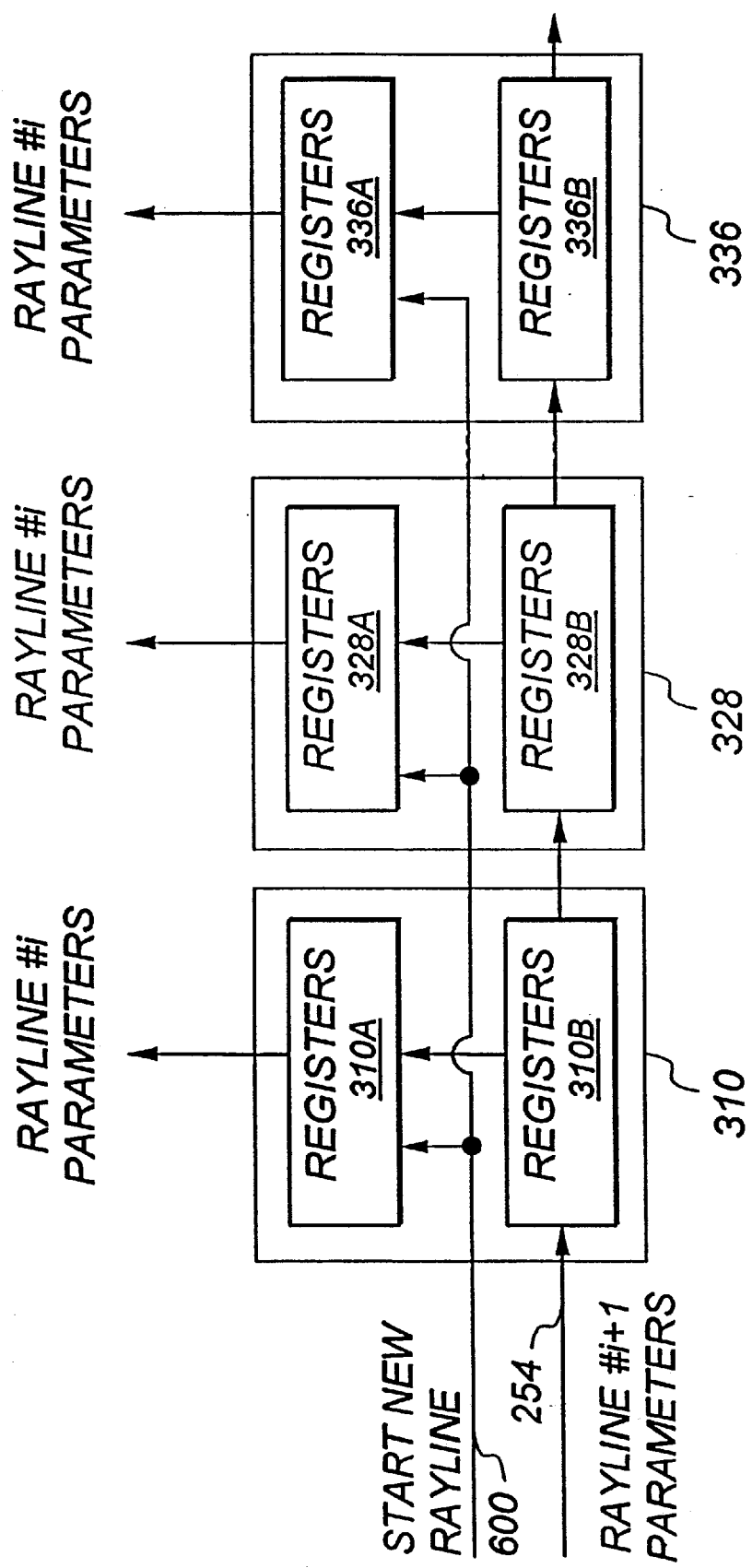
FIG. 6 is a block diagram of the rayline parameters propagation, according to an embodiment of the invention.

It is important to be able to commence acquiring data for a new rayline as soon as a current rayline has been completed. Thus, rayline parameters for the next rayline should be available at module 108 as soon as a current rayline is complete. FIG. 6 is block diagram which illustrates how rayline parameters can propagate according to an embodiment of the invention. In FIG. 6, it is considered that the current rayline being processed is rayline #i. Each rayline is processed according to rayline parameters in register blocks 310, 328 and 336.

As shown in FIG. 6, each register block comprises first and second register sets. For example, register block 310 comprises a first set of registers 310A and a second set of registers 310B. Register blocks 310B, 328B and 336B collectively form a shift register. Serial data received at register block 310B is clocked through until it has propagated through to the end of second register 336B. Register blocks 310B, 328B and 336B may be of different sizes depending on the number of rayline parameters needed in each section. Any or all of register blocks 310, 328 and 336 may be implemented in one or more FPGAs or other software configurable memories so that the size of the register blocks may be varied for different operational modes. Some operational modes may require a different number of rayline parameters than others.

While rayline #i is being processed, rayline parameters for rayline #i+1 are read from memory 222 and are propagated along bus 254 into the second set of registers in each of register blocks 310, 328 and 336. After the rayline #i+1 parameters have been propagated in the last registers block, and when the next rayline begins, a start new line signal 600 on trigger signal bus 252 causes the values in the second set of registers in each register block (i.e. the rayline #i+1 parameters) to be written to the first set of registers. The rayline #i+1 parameters are then used by each section to pre-process rayline #i+1 while rayline parameters for rayline #i+2 are received in the second set of registers.

Software

Software 104 further processes pre-processed data 110 in DMA destination locations 804 in the memory 204 of computer 102 for display on display 116. Software 104 performs a real-time scan conversion on pre-processed data 110 to produce an ultrasound diagnostic image which is stored in memory locations 800 of memory 204. This image may be displayed on display 116. Software 104 may also provide post-processing functions such as frame averaging and edge detection. Software 104 may collect images in memory locations 802 of memory 204 for cineloop visualization. Memory locations 802 hold a series of sequential images which can be displayed in succession by software 104.

Figure 8:
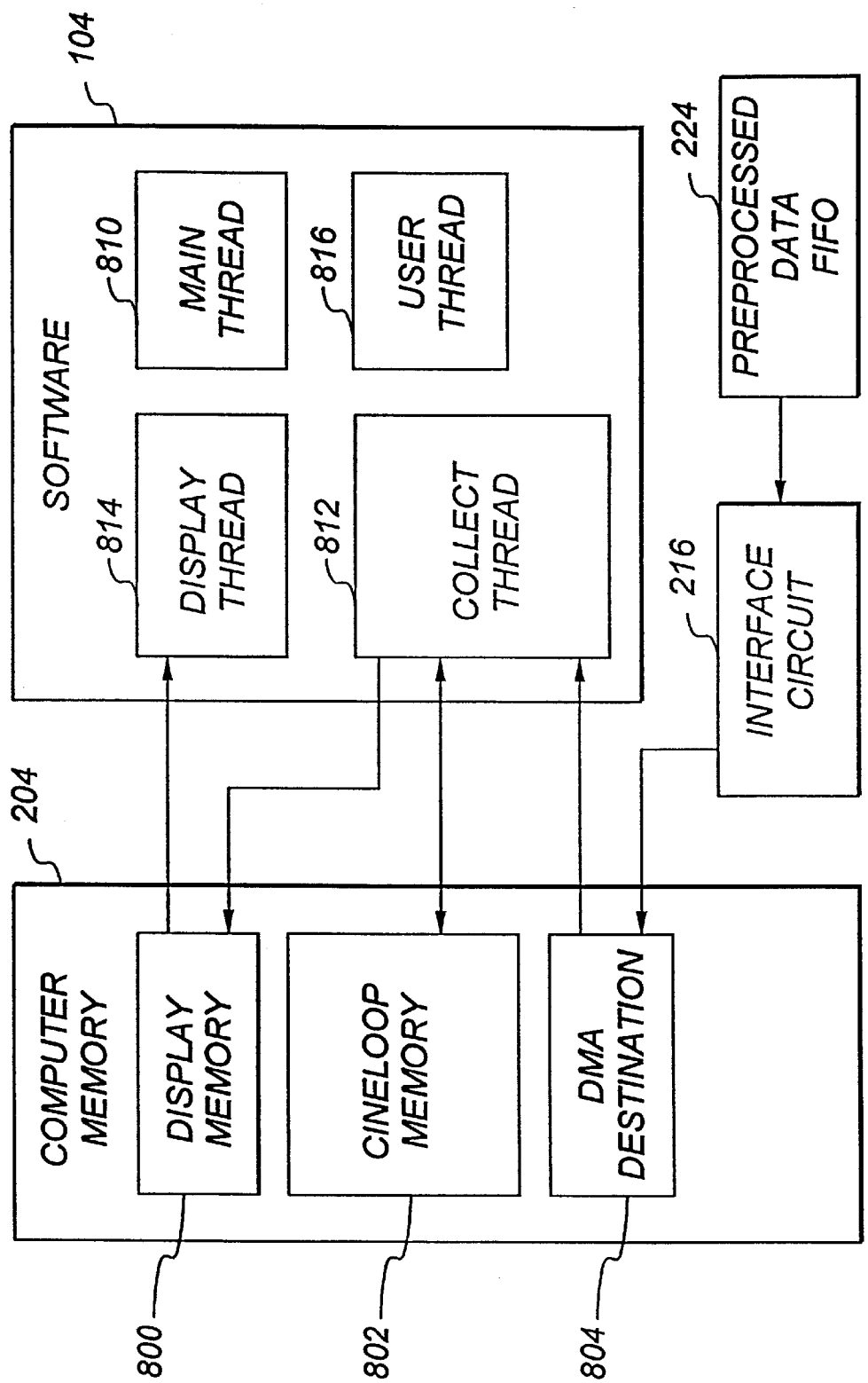
FIG. 8 is an illustration showing the computer software segmentation and use of the computer memory by the computer software for storing raylines.

Software 104 may conveniently comprise 4 threads, or "tasks": a main thread 810, a collect thread 812, a display thread 814 and a user thread 816. The threads are software programs which run together on a multitasking Operating System ("OS") such as Windows NT™ or UNIX. The multitasking OS provides each thread an amount of time during which the thread can operate. To achieve this, the OS takes in consideration the task priority level and the typical allowed time for the thread, also called slice time. FIG. 8 illustrates main components of computer software 104, and shows how those components may use memory 204. For clarity, use of memory 204 by software 104 for storing dispay transform tables and other data is not shown.

Main thread 810 creates the other threads and configures ultrasound module 108. Its priority level is low and it does not need a large slice time.

Figure 10:
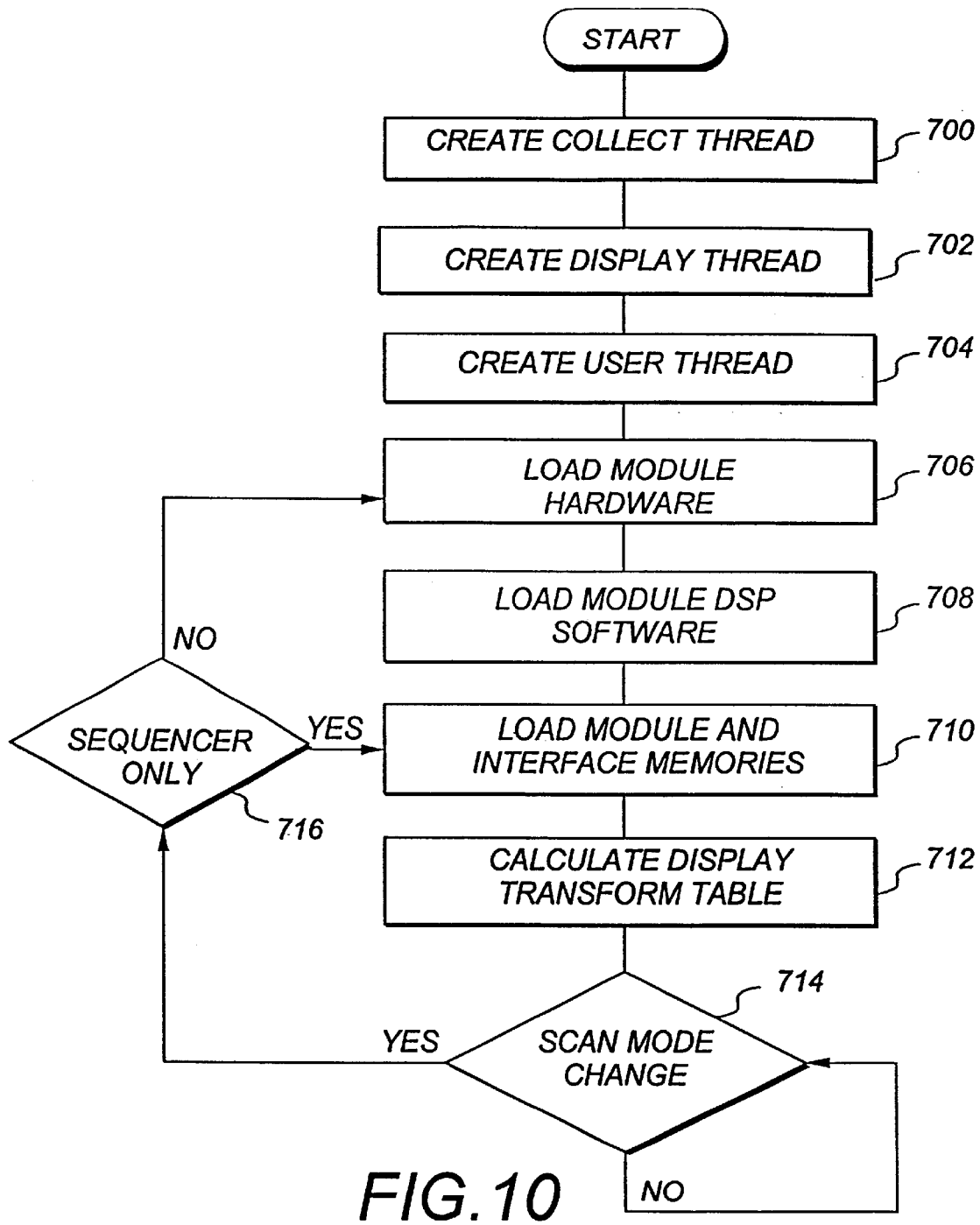
FIG. 10 is a flow diagram of the main software, according to an embodiment of the invention.
Figure 12:
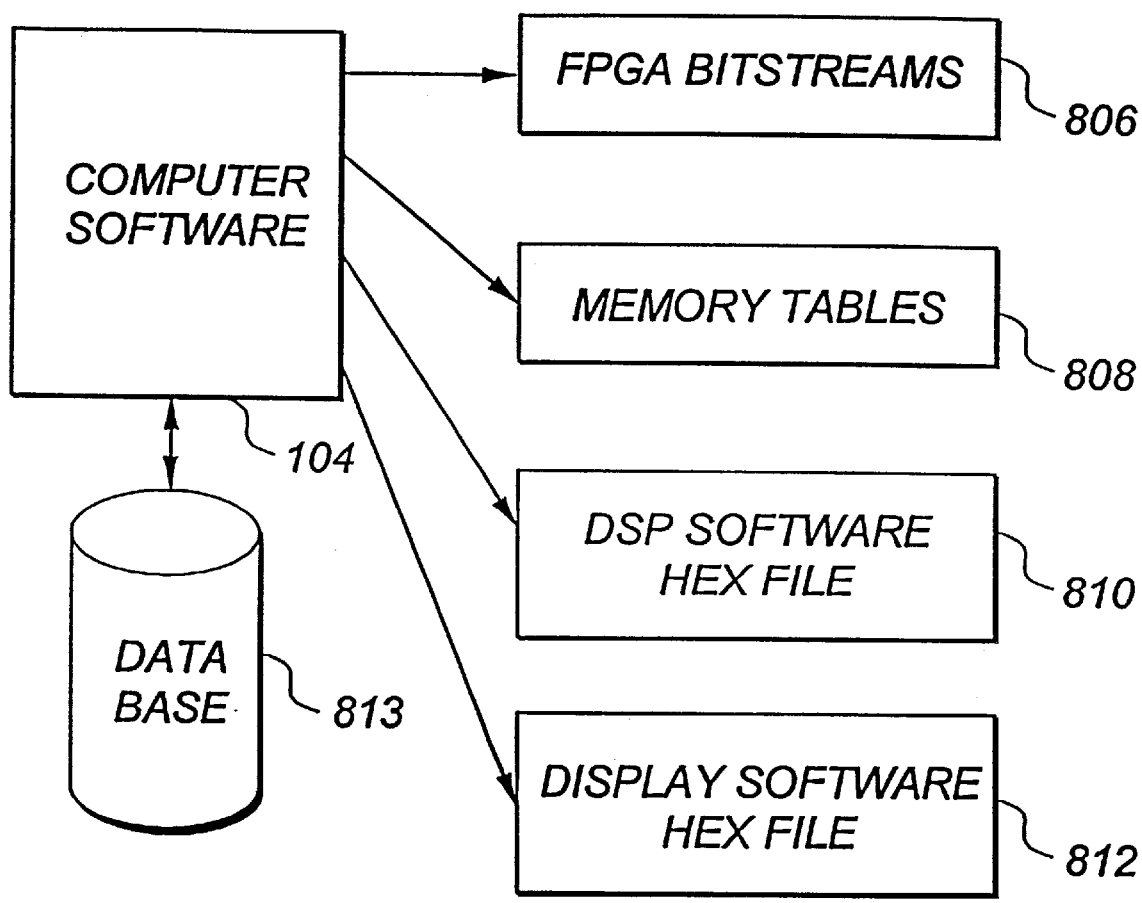
FIG. 12 is a block diagram showing the different elements used for configuring the invention.

FIG. 10 is a flow diagram of main thread 810 of computer software 104, according to a preferred embodiment of the invention. When main thread 810 starts, it first creates collect thread 812 at 700, display thread 814 at 702 and user thread 816 at 704. FIG. 12 is a block diagram showing the different elements which can be used for configuring a system 100.

At 706, main thread 810 loads configuration data into programmable hardware on module 108 and interface board 214 with configuration data according to the starting operational mode of system 100. Software 104 retrieves the configuration data from a storage device accessible to computer 102. The storage device may be a memory, disk drive, or any other repository of computer readable information. For example, configuration data may be retrieved from a database 813 or from one or more configuration files. If necessary software 104 converts the configuration data into bit streams 806 for programming FPGAs, memory tables 808 for storage in memories 222, 340 and 332, a DSP software file 810 and a display software file 812. The configuration data may comprise files, numerical parameters, or any kind of parameters.

The configuration data for each part of module 108 is addressed to the appropriate destination and sent over configuration bus 250. The programmable hardware is composed of the previously described circuits, which may be implemented in programmed FPGAs. Those include the registers 228, 310, 328, 336, sequencers 226, 330, 338, echo unit 400, RF calculator 404, filter 316, summer 318, and delay lines 320. To configure the hardware of ultrasound module 108 the main thread reads configuration files or records from database 813 through I/O devices, such as file storage devices or network devices. These configuration files contain bit streams, which can be downloaded into the FPGAs.

At 708, main thread 810 loads the program memory of DSP 412 through bus 250 with the appropriate digital signal-processing software. The DSP software 414 may include several different DSP programs. To load the memory of DSP 412, main thread 810 reads a configuration file (or a record from database 813) through I/O devices, such as file storage devices or network devices. This configuration file contains the DSP software. The DSP software file 810 preferably contains compiled DSP software 414 to be loaded into the DSP 408 through bus 250.

At 710, the main thread loads the module and interface memories with the contents of memory tables 808 through configuration bus 250. The main thread loads rayline parameters memory 222, receiving section memory block 332, and the transmitting section memory 340. To load these memories, main thread 810 can read configuration files through I/O devices, such as file storage devices or network devices. These configuration files contain pre-computed tables 808. In the alternative, main thread 810 could dynamically recalculate the memory tables.

Thus, by performing steps 706, 708, and 710, the main thread completely configures the real-time digital signal pre-processing performed by the ultrasound module 108 by writing configuration files and tables.

At 712, the main thread calculates display transform tables. The display transform tables are used by the display thread to do the scan conversion in real-time, as described below. Step 712 may include the selection of a display algorithm. This may be accomplished by loading a display software file 812 to be run on computer 102. Display software file 812 contains the display algorithm to be implemented in the display thread. It can be any kind of executable code, stored for example in a dynamically linked library ("DLL"), and will be executed by the CPU 206 on computer 102. An example of a possible display algorithm is described below with reference to FIG. 11.

At 714 main thread 810 enters a loop in which it waits for a user to command changes in the operation of system 100. A user is presented with a user interface which permits the user to select between several different operational modes for system 100 and to select different operating parameters within each possible operational mode. The user can use an input device 118 to generate a change event which specifies a new operational mode for system 100 and/or specifies new parameters for the current operational mode. If a change event occurs, main thread 810 goes to 716 to determine whether the change requires module 108 to be reconfigured for a different operational mode. If the change requires that system 100 be placed into a different operational mode then main thread 810 branches to 706 where it reconfigures the hardware of module 108 and loads new DSP software. This is done by selecting configuration data for the new operational mode from a storage device accessible to computer 102 and loading the configuration data into the hardware or module 108 and the memories on module 108. Changes in which a different operational mode is required include changing to Pulsed Wave Doppler mode, Continuous Wave Doppler mode, CFM (Color Flow Mapping) mode, or Power Doppler mode or changing to a different type of transducer 114.

If the change merely requires different rayline parameters then main thread 810 leaves the operational mode of system 100 unchanged and main thread 810 goes to 710 to load new data into memories 222, 332 and 340 and to recalculate part or all of the display transform tables. The new data may also be stored as configuration data in a storage device accessible to computer 102. No change in the operational mode of module 108 is needed if, for example, a user wants to magnify a specific area of an image, display several images, or use the M-mode. During reconfiguration, display thread 814 keeps the image frozen on display 116 to avoid glitches.

Collect thread 812 controls DMA controller 218 and collects pre-processed data 110 which is received in DMA block 804 of memory 204. When system 100 is not acquiring ultrasound raylines, the collect thread can read back previously collected pre-processed data in a cineloop display mode. Collect thread 812 has a high priority level which permits it to operate in real-time without being unduly interrupted.

In real-time imaging mode, collect thread 812 continuously scans DMA destination memory block 804 to check if new data has been written. If new data is present, collect thread 812 copies the new data to a convenient address in cineloop memory block 802, and to a convenient address in display memory block 800. In frozen imaging mode, the user visualizes the data stored in the cineloop memory block 802. To achieve this, collect thread 812 continuously reads the cineloop memory block 802 and copies the data into the display memory 800, according to a timer synchronization signal. The timer synchronization signal may, for example, be a timer of computer 102.

Display thread 814 performs real-time scan conversion, post-processing, and display. Display thread 814 reads pre-processed data 110 from memory 204 and performs a real-time scan conversion and post-processing to convert the pre-processed data into a diagnostic image. Display thread 814 has a high priority level so that it can operate in real-time without being very interrupted. Display thread 814 may, for example, have the same priority level as collect thread 812. The slice time of the display thread must be larger than the slice time of the collect thread because it requires more computation.

Display thread 814 continuously accesses the display memory 800 to retrieve the data to be post-processed, scan converted, and formatted for display. The display thread also accesses the computer memory 204 to read transform tables. The transform tables contain coefficients for use in mapping the pre-processed data to the image coordinate system.

Display thread 814 may perform other types of calculation to achieve other types of displays, such as scrolling M-mode displays or scrolling pulsed wave Doppler mode displays.

User thread 816 is responsible for providing general input/output device interface and a graphic user interface. User thread 816 retrieves data coming from user input devices, such as keyboard, mouse, control panel, vocal recognition device and generates messages instructing main thread 810 to perform an appropriate action. For example, if a user uses the interface provided by user thread 816 to select an area of a diagnostic image to be magnified then user thread 816 could send a message instructing main thread 810 to reload memory 222 with a new rayline sequence and to recalculate the display tables so as to display a magnified version of the selected area. User thread 816 also retrieves data coming from network devices and storage devices. Concurrently, user thread 816 can output data to network devices, storage devices, and printing devices. The user thread has a low priority level.

Scan Conversion and Display

Figure 9:
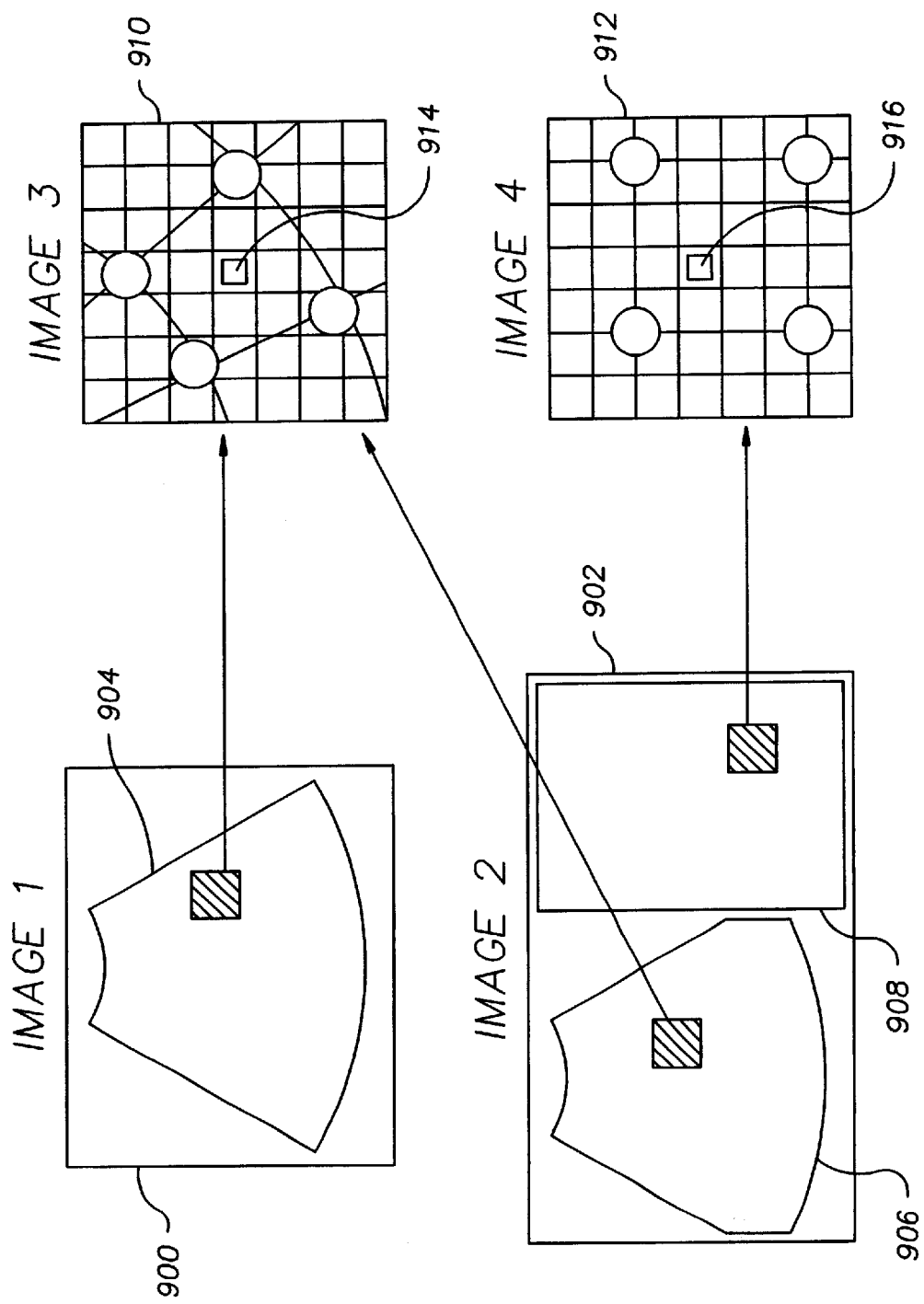
FIG. 9 is an illustration of a scan conversion software, according to an embodiment of the invention.

FIG. 9 illustrates a scan conversion method, according to an embodiment of the invention. The scan conversion algorithm converts pre-processed data 110, which has a coordinate system defined by the geometry of the transducer 114 and the waveforms used to drive transducer 114 into a diagnostic image having a rectangular coordinate system. The coordinate system of pre-processed data 110 is typically a polar coordinate system but may be a rectangular coordinate system in some cases where transducer 114 is linear. The scan conversion algorithm, implemented in display thread 814, builds a diagnostic image by sequentially calculating colors for pixels in the image. For convenience, gray levels will also be called colors.

Image 1 is an illustration of a B-mode diagnostic image 900. Diagnostic image 900 contains a scan area 904. Each pixel in diagnostic image 900 has a color which can be determined as a weighted average of four pre-processed image points. Image 3 shows a magnified part 910 of the diagnostic image 900. In Image 3, the grid shows the diagnostic image pixels placement. The color of the central pixel 914 can be calculated as a weighted average of the four closest pre-processed data points 915, 916, 917, and 918. As a result, scan converter algorithm needs four interpolation coefficients to calculate a diagnostic image pixel's color. The coefficients, which are stored in the transform table specify for each pixel the weight to be given to each of the four nearest pre-processed data points. Outside of scan area 904, the interpolation coefficients may be set to zero.

Image 2 shows a dual mode diagnostic image 902. This configuration can for example be used in M-mode or Pulsed Doppler mode. Diagnostic image 902 is composed of two scan areas 906 and 908. Scan area 906 is like the scan area 904 in B-mode. Scan area 908 represents linear lines displayed vertically as a function of time. Each pixel of the diagnostic image 902 can be calculated as a pondered average of four pre-processed image points, the same way described above in relation to diagnostic image 900.

Image 4 shows a magnified part 912 of the right scan area 908. The color of central pixel 916 may be calculated as a weighted average of the four closest pre-processed data points 920, 921, 922, and 923. As a result, in all modes, the scan converter algorithm needs four interpolation coefficients to calculate the color of a diagnostic image pixel. Outside of the scan areas 906 and 908, the interpolation coefficients can be set to zero.

Using that method, any presentation can be achieved using a four points interpolation method for scan conversion. The interpolation coefficients can be stored in pre-calculated tables.

Figure 11A:
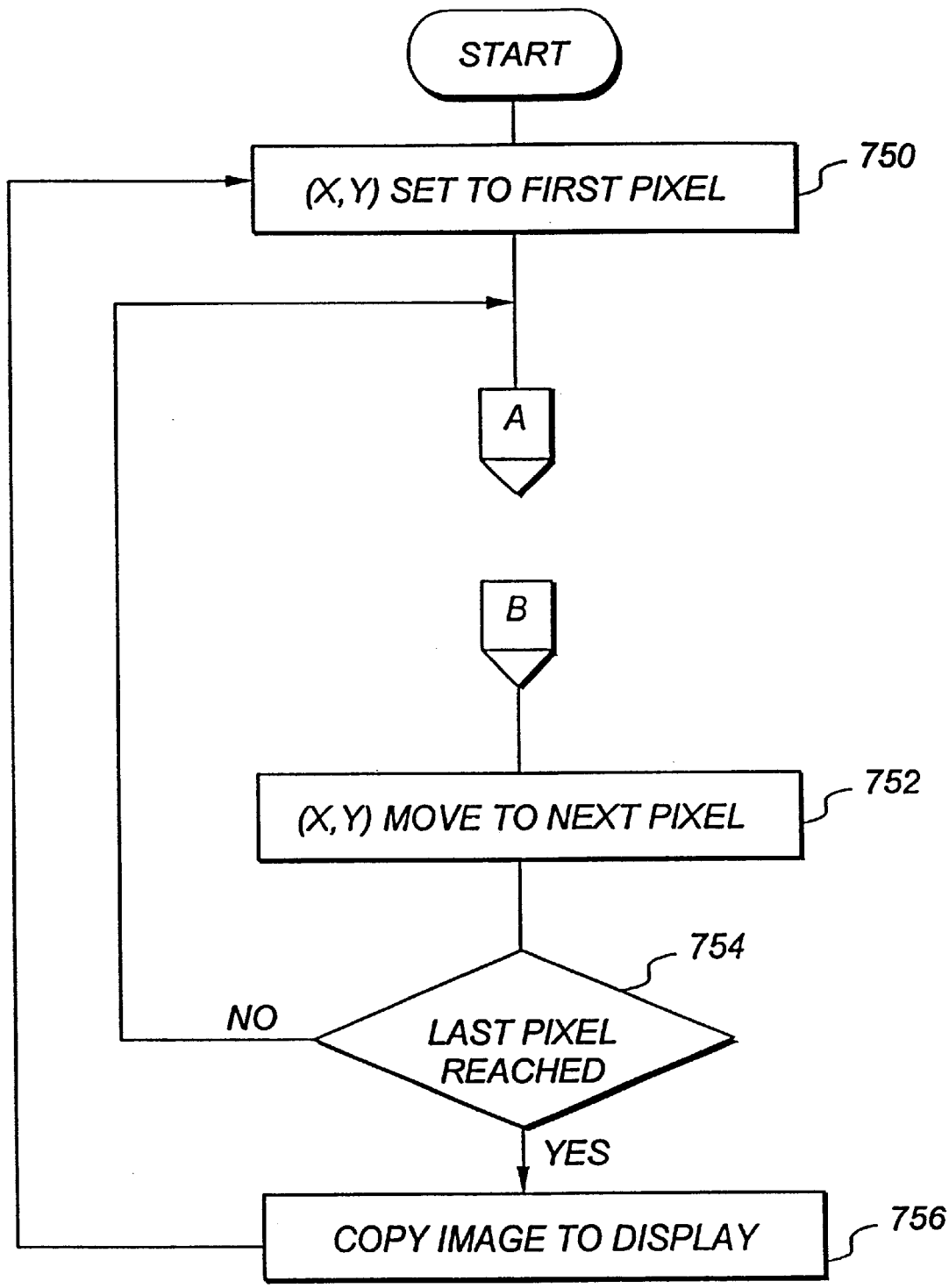
FIG. 11 is a flow diagram describing a scan conversion method, according to an embodiment of the invention.
Figure 11B:
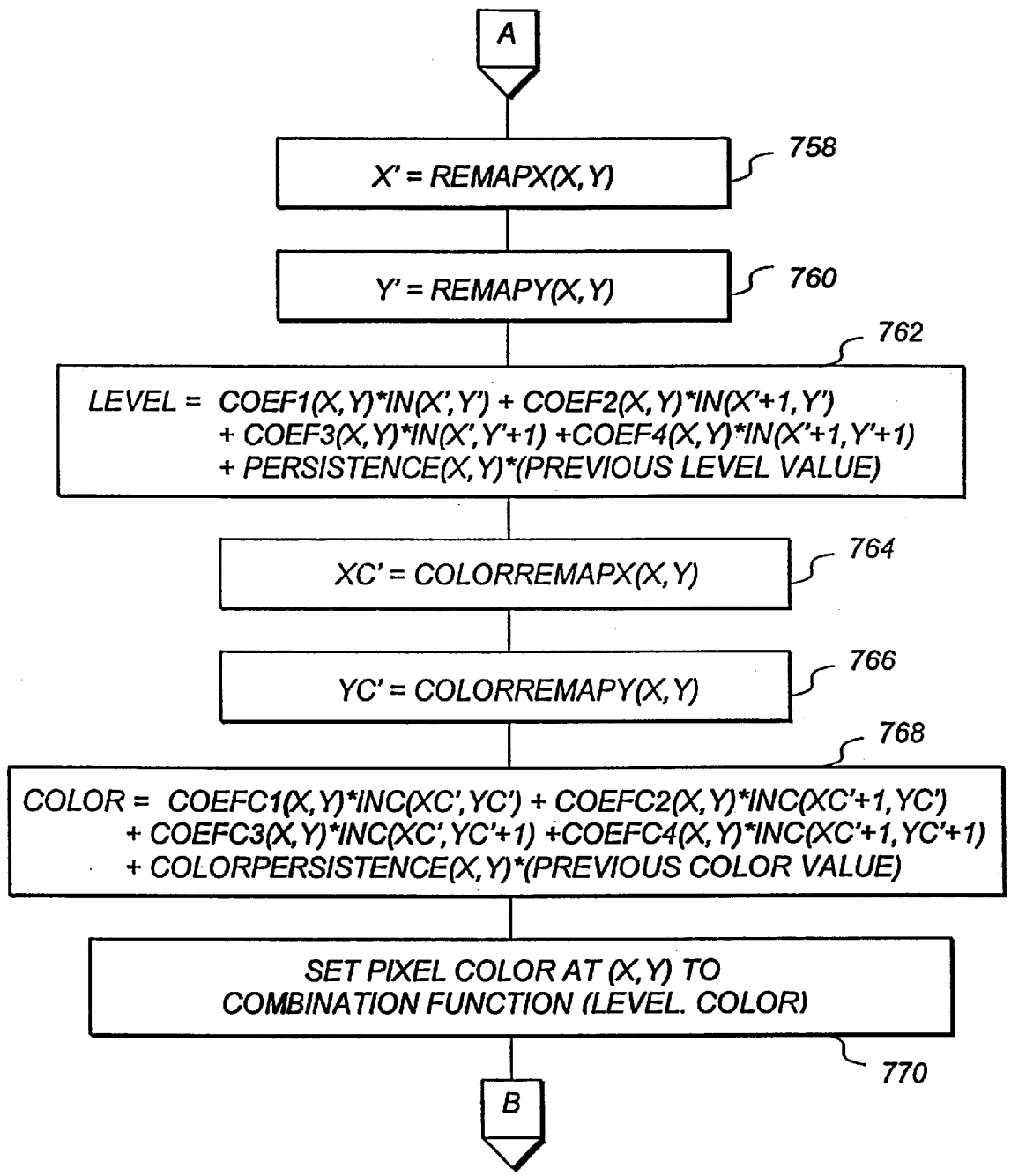

FIG. 11 is a flow diagram showing a possible implementation of display thread 814. Display thread 814 generates a display which shows echo-level and color velocity. Display thread 814 computes the color for each pixel of the diagnostic image. To achieve this, display thread 814 typically computes each pixel's color by doing the scan conversion and persistence algorithm, and transfers the diagnostic image to display adapter 210 for display on video display 116.

At 750, display thread 814 initializes a pixel counter (X,Y). After the computation of the color for pixel (X,Y), display thread 812 reaches 752 and moves to the next pixel. At 754, display thread 814 tests to see if the diagnostic image computation is completed. If the diagnostic image computation is completed, the display thread copies the diagnostic image to display adapter 210 at 756, and then starts to compute the next diagnostic image. Before copying the diagnostic image to display adapter 210, display thread 814 mixes user display data and diagnostic image. The user display data is customizable and can show general information such as current time, probe frequency, or user text such as part names or patient name.

The maximum frame rate is fixed by the maximum rate at which display thread 814 can generate the image to display. This depends on the speed of computer 102, the size of the diagnostic image, and the pixels' color computation software. With 256 kilobytes of pre-processed data per image, and a 800 per 600 pixels display, rates of 30 images per second can be reached on a Pentium™ processor with MXX instruction set clocked at 450 MHz.

At 758 and 760, (X',Y') are calculated as remapping coordinates of (X,Y). (X',Y') designates the coordinates of the echo-level reprocessed data. The echo-level reprocessed data IN(X',Y') is the echo-level sample Y' on rayline X'. As discussed above in relation to FIG. 9, the scan converted echo-level for pixel (X,Y) can be calculated as a weighted average of IN(X',Y'), IN(X'+1,Y'), IN(X',Y'+1), IN(X'+1, Y'+1). Furthermore, to accomplish image persistence, it is possible to use a coefficient called PERSISTENCE(X,Y), which is used as a temporal coefficient. At 762, the display thread calculates the echo level for pixel (X,Y) according to the following formula:

$$\text{LEVEL VALUE} = COEF1(X, Y) * IN(X', Y') +$$
$$COEF2(X, Y) * IN(X' + 1, Y') +$$
$$COEF3(X, Y) * IN(X', Y' + 1) +$$
$$COEF4(X, Y) * IN(X' + 1, Y' + 1) +$$
$$PERSISTENCE(X, Y) *$$
$$(\text{PREVIOUS LEVEL VALUE})$$

At 764 and 766, (XC',YC') are calculated as remapping coordinates of (X,Y).(XC',YC') designates the coordinates of the color reprocessed data. The color pre-processed data INC(XC',YC') is the color sample YC' on rayline XC'. Applying the discussion of FIG. 9 to the color image, the scan converted color for pixel (X,Y) can be calculated as a pondered interpolation of INC(XC',YC'), INC(XC'+1,YC'), INC(XC',YC'+1), INC(XC'+1,YC'+1). The color sample INC(XC',YC') can be a table function of the reprocessed velocity average and variance data for sample YC' on rayline XC'. To accomplish color image persistence, it is possible to use a coefficient called COLORPERSISTENCE(X,Y), which is used as a temporal coefficient. At 768, the display thread calculates the color for pixel (X,Y) according to the following formula:

$$\text{COLOR VALUE} = COEFC1(X, Y) * INC(XC', YC') +$$
$$COEFC2(X, Y) * INC(XC' + 1, YC') +$$
$$COEFC3(X, Y) * INC(XC', YC' + 1) +$$
$$COEFC4(X, Y) * INC(XC' + 1, YC' + 1) +$$
$$COLORPERSISTENCE(X, Y) *$$
$$(\text{PREVIOUS COLOR VALUE})$$

The REMAPX, REMAPY, COLORREMAPX, COLORREMAPY, COEF1, COEF2, COEF3, COEF4, COEFC1, COEFC2, COEFC3, COEFC4, PERSISTENCE, and COLORPERSISTENCE tables can be pre-calculated or recalculated by the main thread each time a scan mode change occurs. The PERSISTENCE and COLORPERSISTENCE coefficients are automatically set to zero on M-mode areas, such as scan area 908.

At 770, the display thread calls a combination function which combines the echo-level and color values to compute the color for the pixel (X,Y). The combination function can use thresholds and tables to determine the resulting pixel color. The computation done in FIG. 11 can also be changed to achieve additional post-processing features, such as edge enhancement.

Networking

Computer 102 is preferably connected to other computers on a network. Software 104 preferably has networking capabilities which permit it to exchange information on a network of ultrasound devices, as it will be described below. This may be accomplished by providing a network adapter 212 coupled to motherboard 202 through a bus 234 together with suitable networking software. Bus 234 may be, for example, a PCI bus. Network adapter 212 connects system 100 to a LAN (Local Area Network) or a WAN (Wide Area Network) as explained below.

Figure 7:
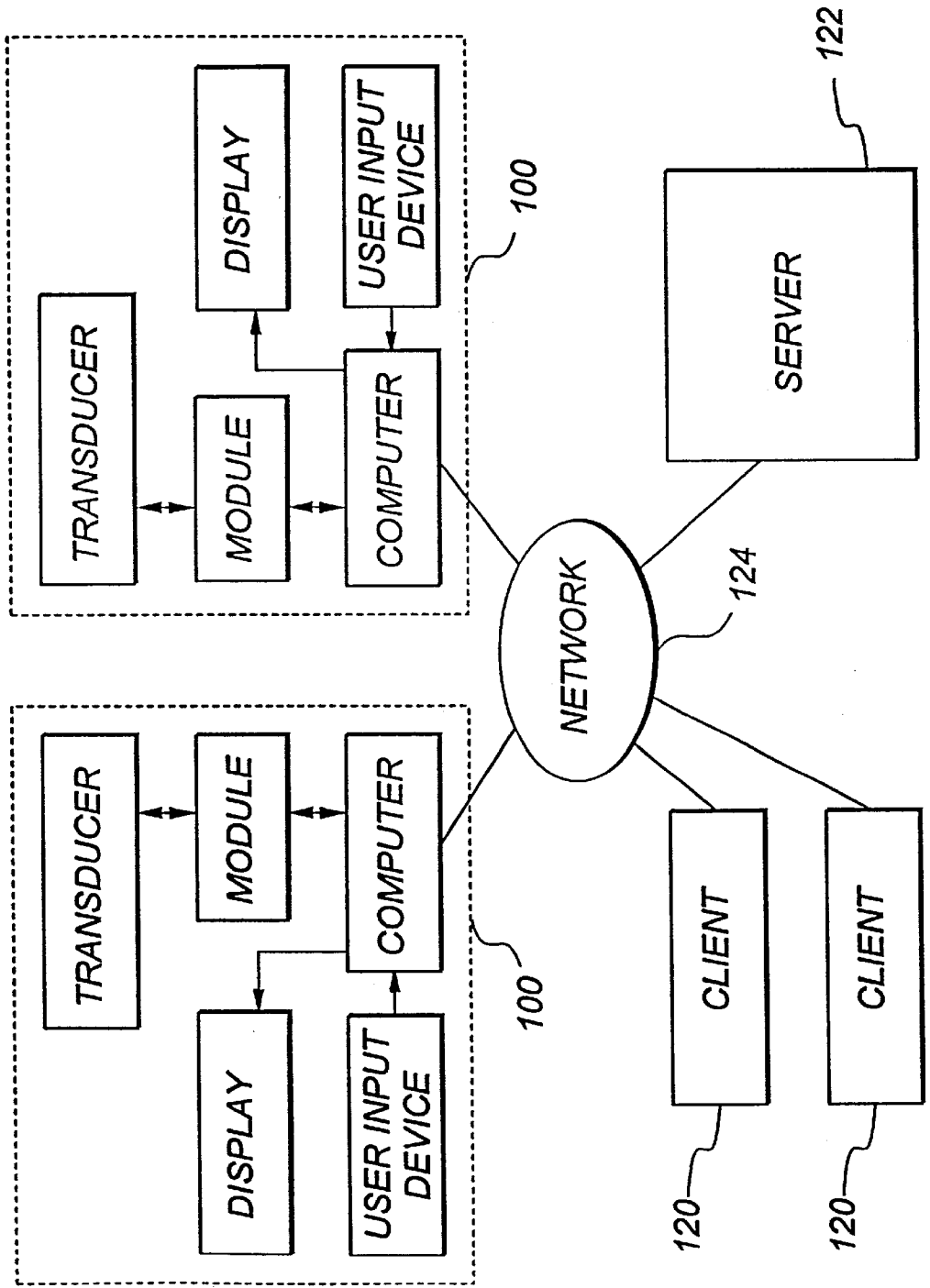
FIG. 7 is a block diagram of an ultrasound devices network configuration, according to the invention.

FIG. 7 is a block diagram showing two systems 100 according to the invention connected to a network 124. Two additional clients 120, and one server 122 are also connected to network 124. A plurality of ultrasound imaging systems can coexist on a LAN (Local Area Network) or a WAN (Wide Area Network). Each ultrasound imaging system can be linked to one server and indirectly to other client machines to provide various services, such as report generation, tele-exam, remote control, and patient database administration.

The ultrasound imaging systems 100 have network hardware and software capabilities. Because systems 100 include conventional computers 102 they can be networked using off the shelf networking cards and suitable network software. Additional clients 120 can be computers, programmed with specific client software. Clients 120 may generate diagnostic reports, archive diagnostic images, remote control or examine the ultrasound imaging systems 100. Server 122 may be a computer, programmed with specific server software. The purpose of server 122 is to assign addresses to all the clients on the network, and to control the network data transfers. Furthermore, a patient database may be implemented on the server 122 to store diagnostic images and patient information. Network 124 can be a combination of LAN (Local Area Network) and WAN (Wide Area Network). Network 124 may support various protocols, such as Internet protocols and file transfer protocols.

Server 122 can communicate with each of clients 120 and systems 100. Software in clients 120 can converse with server 122 to indirectly access one or several ultrasound imaging systems 100 on network 124. Clients 120 can retrieve diagnostic images from or send previously saved diagnostic images to ultrasound imaging systems 100. Clients 120 may also remotely control ultrasound imaging systems 100.

The provision of clients 120 on network 124 permits systems 100 to be used for diagnostic purposes while clients 120 can be used to generate reports, update patient databases and perform other tasks which do not involve the acquisition of new images. Diagnostic images may be transferred between systems 100 and clients 120 by using FTP (File Transfer Protocol) client software on client machines 120 and 100, and FTP server software on server 122. When an ultrasound imaging system 100 has a diagnostic image available for upload, it can send a request to the server and the server can then retrieve the image and store it on a storage device at server 122. Clients 120 may request the server 122 to periodically send them the most recent diagnostic image for a specific ultrasound imaging system 100.

Example Applications

The use of a fully configurable RF calculator 404 and of a software-controlled DSP 408 enables the implementation of powerful and complex digital signal-processing algorithms. One application of signal-preprocessing unit 312 is velocity imaging. Signal-preprocessing unit 312 can be set up to perform any of the following algorithms in real-time: CFM (Color Flow Mapping) imaging algorithms, Power Doppler imaging algorithm, Pulsed Wave Doppler imaging algorithms, Continuous Wave Doppler imaging algorithms. To implement these velocity algorithms, RF calculator 404 is used to perform RF data demodulation, filtering, and averaging. This may be done by configuring RF calculator 404 as a digital TAP filter with pre calculated coefficients. For example, RF calculator 404 may be configured as a 16-TAP filter with fixed coefficients selected to provide demodulation, filtering and averaging. Configuring RF calculator 404 as a multi-tap filter and selecting suitable coefficients to cause the filter to perform demodulation filtering and averaging is a matter of routine to those skilled in the art.

The resulting demodulated, filtered, and averaged data is called Doppler signal. The Doppler signal data rate is lower than the RF data sampling frequency. The Doppler signal is forwarded to DSP 408 through the pre-DSP FIFO 406. The DSP software 414 performs an auto-correlation algorithm for CFM or Power Doppler imaging, or a Fast Fourier Transform (FAT) algorithm for Pulsed Wave Doppler and Continuous Wave Doppler imaging.

FIGS. 13A through 13E show examples of configurations of the major programmable components of system 100 for different operational modes of system 100. Five very different modes of operation are briefly described to give an idea of the extensive versatility and programmability possible in systems according to the invention. Of course, numerous other modes of operation could also be implemented, whether they are established or new experimental imaging techniques.

Figure 13A:
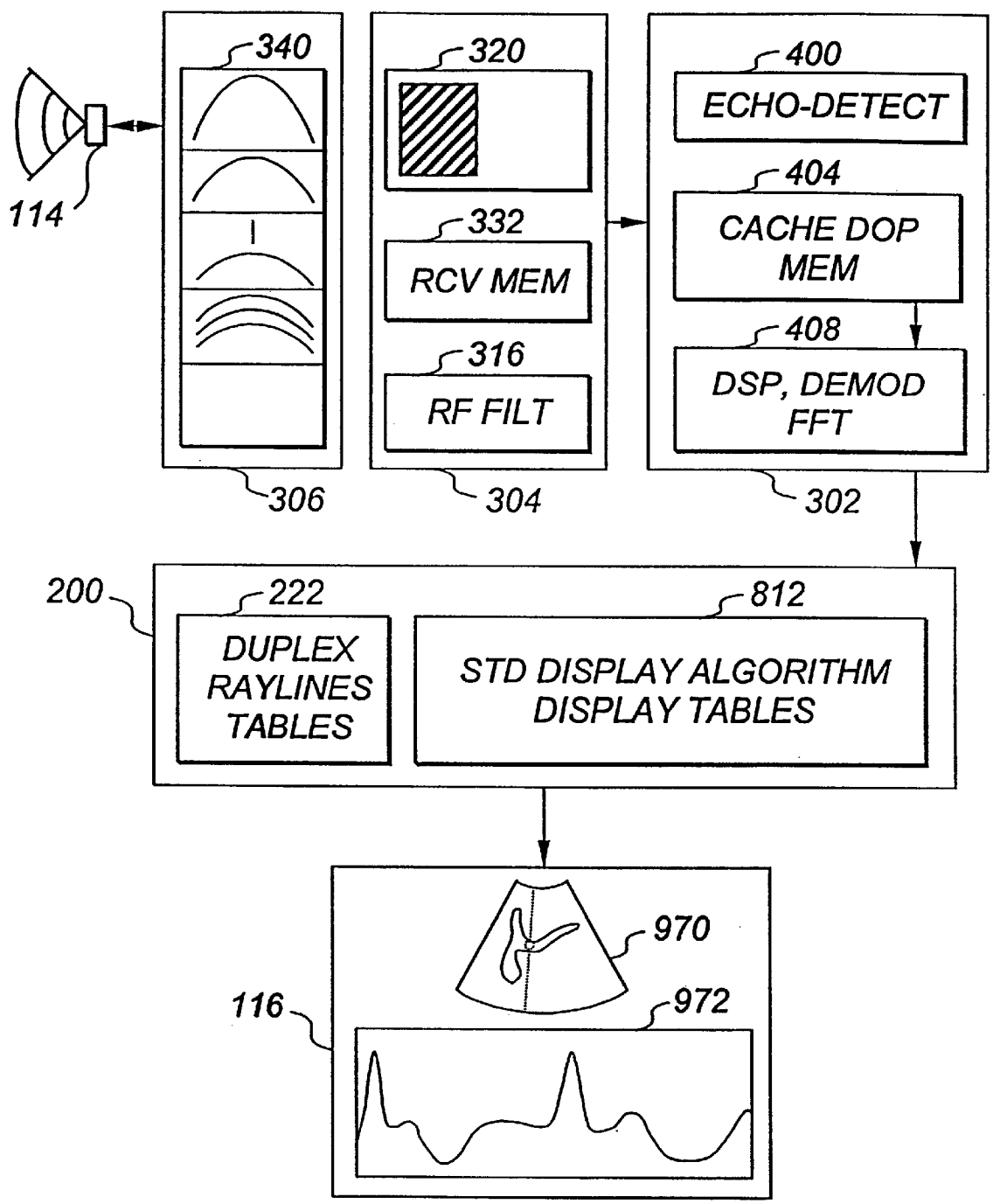
FIG. 13 shows examples of configuration of the major programmable components for different modes of operation of the invention; and, FIG. 14 is an ultrasound system for producing ultrasound images according to the second embodiment of the invention. The accompanying figures are schematic in nature and omit for clarity some elements which are known, or which can be readily inferred from the following description and appended drawings, by those skilled in the field of designing ultrasonic imaging systems.

FIG. 13A is an example of duplex configuration with a convex transducer. In this mode, a B-mode image 970 is shown in real-time on display 116, along with a pulsed-Doppler image 972, which is a spectrum representation of the blood flow velocity in a specific region of the B-mode image. To achieve this mode, standard transmitting beams are loaded into memory 340. Memory 340 can contain a specific multiple-pulses transmit sequence for the Doppler line. Delay lines 320 are provided by FPGAs configured to provide synchronous RAM-based registers, using the maximum number of channels, and not necessarily allowing large delays because those are not needed for a convex probe configuration. Receive memory 332 can contain different focusing data, gain compensation data, filtering data for the B-mode image and Doppler line. RF filter 316 can be loaded with configuration data which configures it to provide a 32-tap dynamic digital high-pass filter. Echo-level preprocessing unit 400 is loaded with data which configures it to provide echo detection circuitry, as described in FIG. 4A, which comprises echo redressing and fixed low-pass filtering. Signal-preprocessing unit 402 has two main programmable elements: RF calculator 404 and DSP 408. To process the Doppler line, the RF calculator 404 is configured as a simple cache memory, which saves for example 256 samples in the Doppler region of the Doppler rayline. DSP 408 is configured to compute a complex demodulation, which can be reduced to digital filtering, of the cache memory values, followed by a Fast Fourier Transform (FAT) of the demodulated value, to be shown on the screen. Memory 222 is loaded with rayline parameters for the duplex mode. A standard display algorithm, as described below with reference to FIG. 9 and FIG. 11, may be used. Software 104 computes the display tables to match a display configuration as selected by the user. When a user changes the position of the Doppler line, software 104 only reloads the rayline memory 222.

Figure 13B:
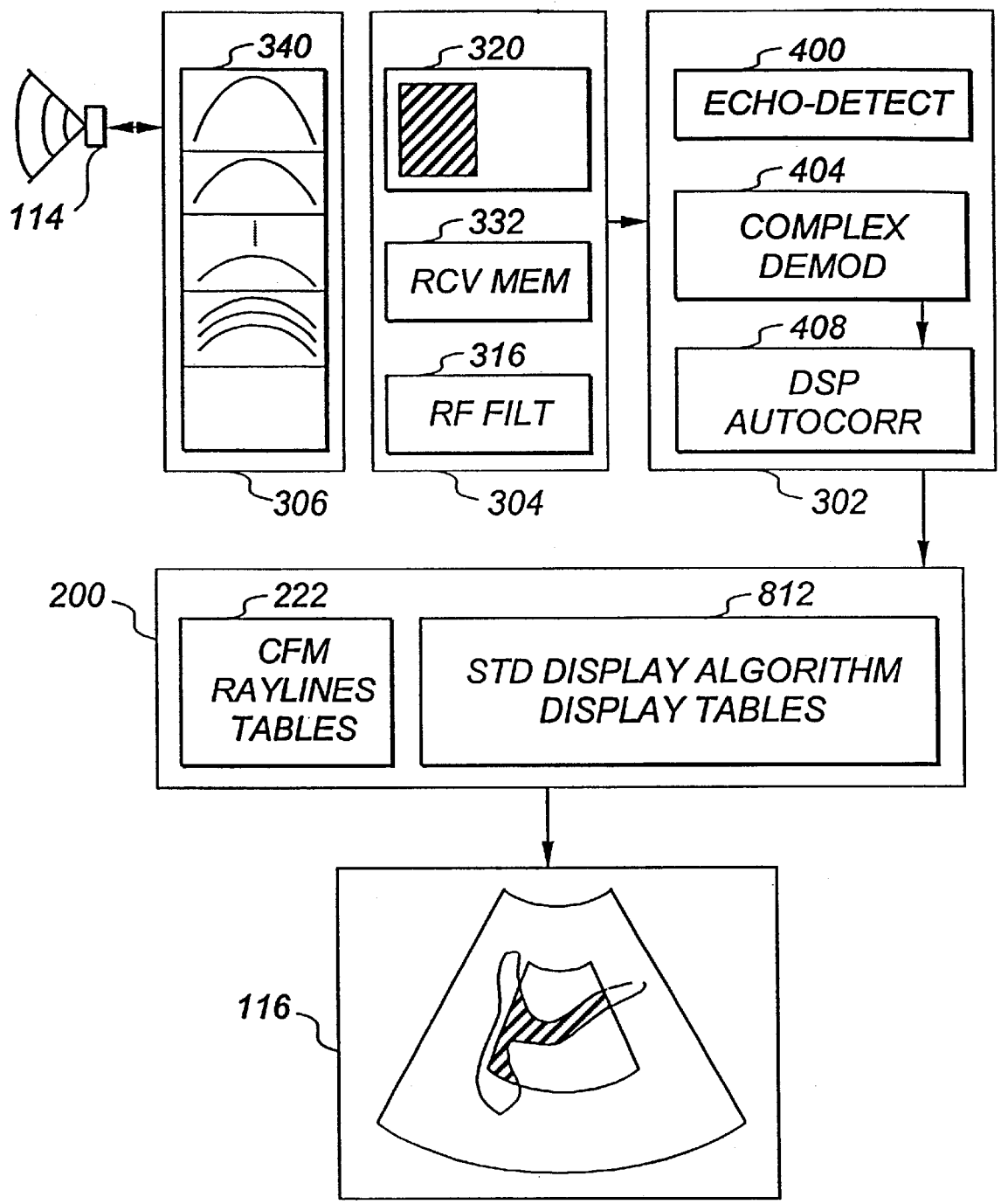

FIG. 13B shows a system 100 configured for B-mode color flow mapping with a convex transducer. Color flow mapping is a color representation of blood flow speed and variance in a specific region of the image. Transmitting section 306 and receiving section 304 are loaded with the same values as in FIG. 13A. RF calculator 404 is configured to provide a circuit which computes a complex demodulation of the input RF data in real-time. DSP 408 is configured to compute an auto-correlation of the demodulated values. The result of this auto-correlation gives speed, variance and power information, in the pre-processed data 110. Unlike the pulsed-Doppler mode, velocity information has to be performed on numerous points. Thus, moving the complex demodulation from the DSP 408 to the RF calculator 404 leaves enough power to the DSP 408 for processing the color algorithm in real-time. Memory 222 contains rayline parameters for the color flow mapping mode. A standard display algorithm, as described below with reference to FIG. 9 and FIG. 11, may be used. Software 104 computes the display tables to match a display selected by a user. Triplex mode, which is like the duplex mode, but with a color image, can easily be implemented. In triplex mode, the RF calculator 404 is configured to perform both complex demodulation and caching of the pulsed-Doppler region. DSP 408 performs auto-correlation for the color image, and a complex demodulation with FAT only for the cache memory pulsed-Doppler values. All these operations can be performed in real-time. The frame rate will be lower simply because more raylines need to be transmitted and received.

Figure 13C:
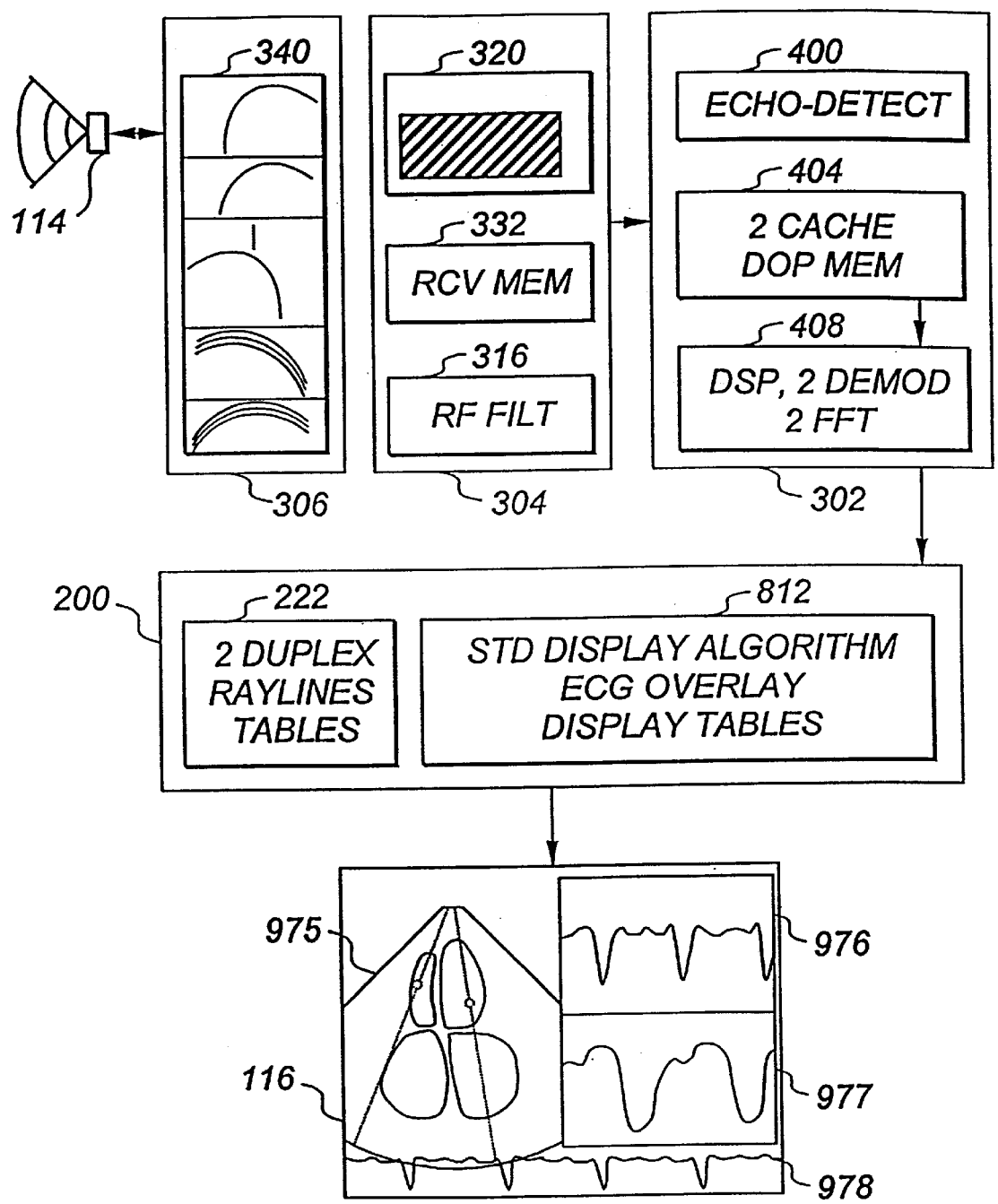

FIG. 13C shows system 100 configured to provide dual pulsed-Doppler imaging using a phased array transducer. In this mode, a B-mode image 975 is shown in real-time, along with two screen images 976, 977 which contain two different pulsed-Doppler spectrums of two different regions of the B-mode image. The use of a phased array transducer makes necessary angular transmitting and receiving sequences. To achieve this, transmitting memory 340 is loaded with angular transmit sequences for the B-mode image, and multiple-pulses angular transmit sequences for the pulsed-Doppler lines. Delay lines 320 can be configured in a different way from FIG. 13A and FIG. 13B. To use phased arrays, the system needs large delays. To increase the maximum delays, the FPGAs which provide delay lines 320 can be programmed to provide synchronous RAM-based registers, using fewer channels, but which provide the large delays as needed for focusing with a phased array. Memory block 332 and RF filter 316 are the same as in FIG. 13A. RF calculator 404 can be programmed to provide two cache memory blocks, and DSP 408 can perform complex demodulation and FAT on values cached in the two cache memory blocks. Memory 222 is loaded with the rayline parameters for dual pulsed-Doppler mode. A standard display algorithm, as described below with reference to FIG. 9 and FIG. 11, may be used. To add an ECG trace 978, the standard display algorithm may be modified to mix the ECG trace and the diagnostic image before displaying the result on the display. Software 104 computes display tables to match the screen configuration selected by a user.

Figure 13D:
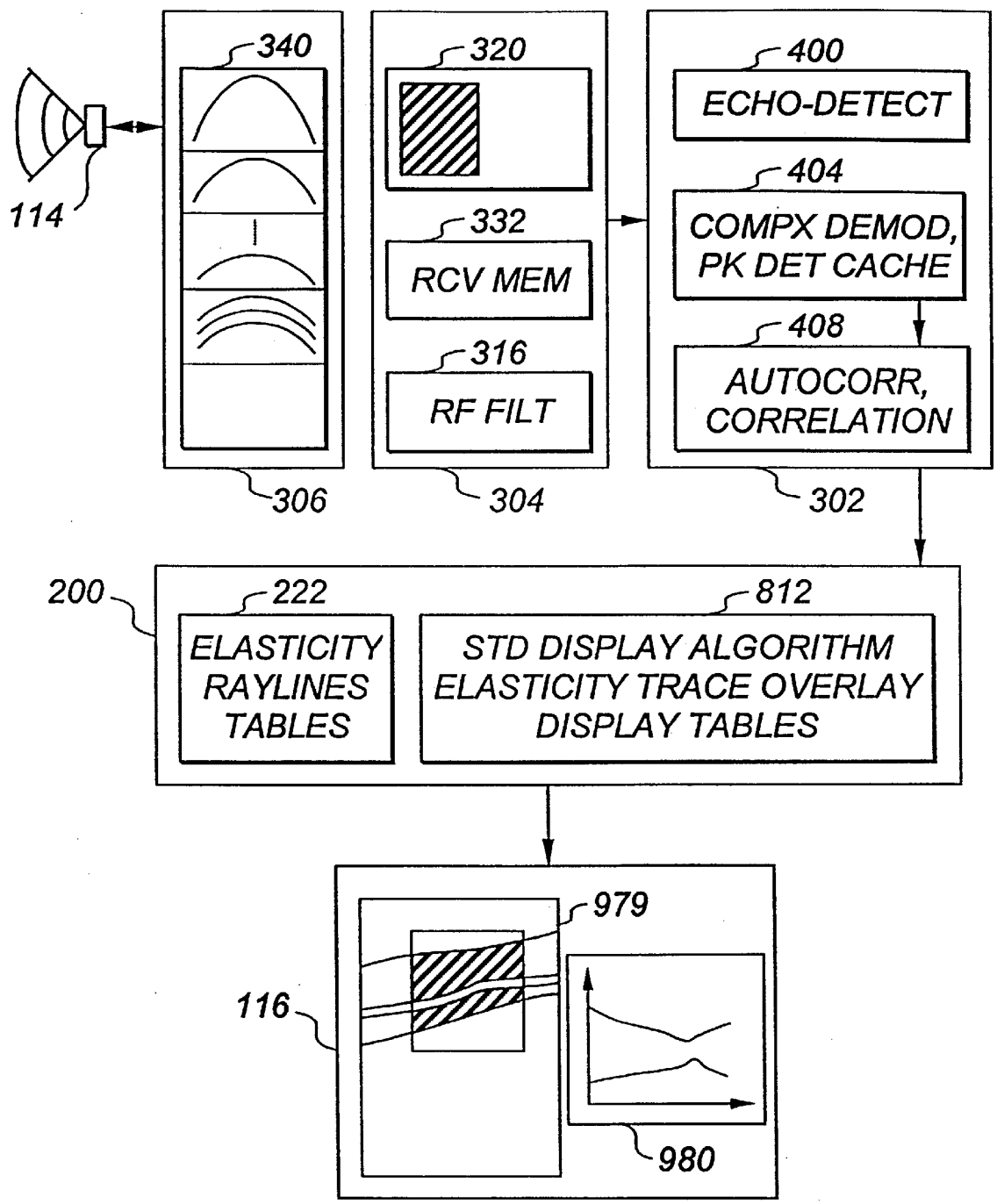

FIG. 13D is an example of an imaging mode for displaying variations in tissue elasticity using a linear transducer. In this experimental mode, a B-mode with color diagnostic image 979 is shown, along with a graph 980 which shows the elasticity of the carotid walls, as described in U.S. Pat. No. 5,579,771 to Bonnefous. To achieve this mode, transmit unit 306 and receive unit 304 can be configured as in FIG. 13A. RF calculator 404 is configured to process a complex demodulation, for color imaging, and a peak detection with cache memory for carotid wall detection and caching. DSP 408 computes an auto-correlation of the demodulated values, for color imaging, and a correlation of contiguous cache memory peak-detected lines, along with wall thickness calculation. Since the amount of computation for elasticity measurements and color imaging are comparable, this can still be achieved in real-time by system 100. The primary factor limiting the frame rate will be the physical time necessary for transmitting and receiving acoustic signals 115 and 115A. Memory 222 is loaded with rayline parameters for the elasticity mode. A standard display algorithm may be used. To add the real-time elasticity trace in another part of the display, the standard display algorithm can be modified to draw the elasticity trace on the diagnostic image before copying the result on the display. Computer software 104 computes the display tables as desired by the user, so that any display configuration can be accomplished.

Figure 13E:
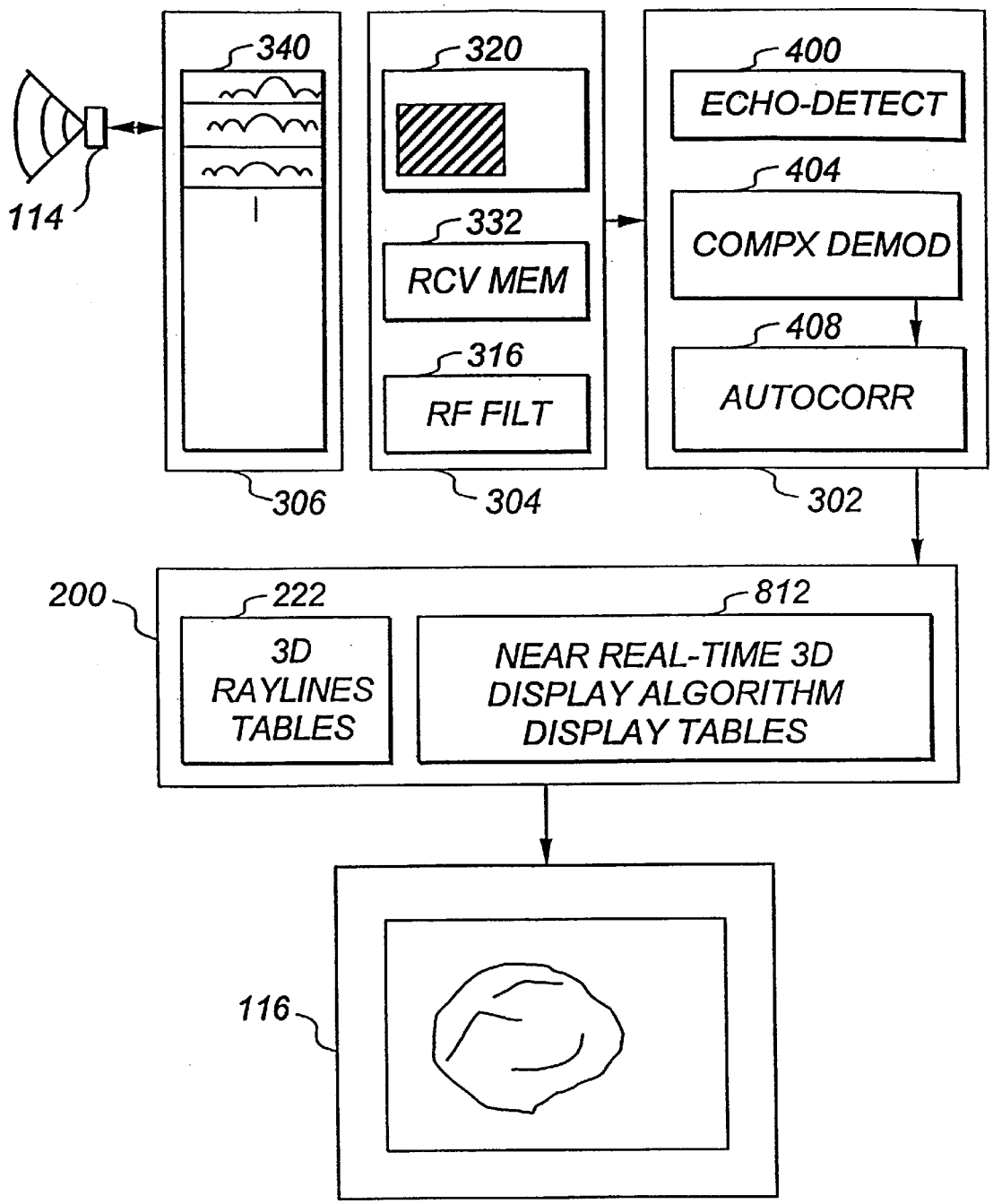

FIG. 13E is an example of 3D real-time imaging with the present invention. This mode uses a transducer having a 2D array of transducer elements, to allow transmit and receive sequences in any spatial direction. The raylines are processed to show a surface-rendered 3D image. The 3D reconstruction can be applied to color data, as well as echo-level data, depending on the display software. To transmit 3D focused raylines, transmitting memory 340 is loaded with computed delays for the specific transducer. The FPGA which provides delay lines 320 can be programmed to provide synchronous RAM-based registers. The number of channels can be adjusted to allow the delay lines to provide the delays necessary with the 3D transducer. Preprocessing unit 302 is configured for standard echo-level and color imaging, as described in FIG. 13B. Memory 222 contains rayline parameters for the 3D mode. The display algorithm will be a 3D reconstruction algorithm. 3D reconstruction algorithms can be processed in real-time or near real-time on standard computers with specific video cards.

Another mode for generating 3-D images requires a position sensor on a transducer 114. A transducer 114 having a 1-D array of elements may be used. If the transducer is moved so that consecutive images show different parts of the patient's body then optional software running on computer 102 could generate 3D images of the patient's body by assembling consecutive images, considered as slices. To achieve this, the software can use position information sent by a sensor (not shown) which records the position and orientation of probe 114, or perform a correlation algorithm on subsequent images.

Thus, all the example applications presented in FIGS. 13A through 13E can be obtained by simply loading the main parts of ultrasound module 108 and memory 204 with different data which can be retrieved from a database 813 or a suitable configuration file. Also, with the digital signal-preprocessing unit 312 architecture and the optimized display algorithm, all these modes can be operated in real-time. This gives an idea of how easy it is to implement different transducers, real-time imaging modes and different screen configurations without changing the hardware of system 100.

From the above description one can appreciate that a system 100 according to the invention which is software configurable provides several advantages over conventional diagnostic ultrasound systems which are hard wired to provide specific functions. Using hardware programmable blocks in the ultrasound module allows the computer software to fully control and configure every operation of the ultrasound module, from the beam-forming to the preprocessing. Thus, the ultrasound imaging system is entirely programmable, and versatile. New real-time imaging algorithms, new focusing methods as well as new calculations, new networking protocols can be implemented without changing the system's hardware.

Using an ultrasound module 108 for dynamic beam-forming and preprocessing facilitates real-time imaging in all modes. The use of a computer as a controller, user interface and display system makes development of software 104 much more simple than would be the case if software 104 were required to run on non-standard custom hardware. An off-the-shelf operating system can be used to take advantage of the numerous existing tools and libraries to build a friendly and familiar user interface, handle input/output devices and network protocols. Furthermore, the number of electronic boards is reduced thanks to the software, which makes manufacturing and maintenance easier.

System 100 permits each rayline in an image to be processed differently. Different calculations can be performed for each rayline. Furthermore, specific dynamic focusing and filtering techniques may be applied to each rayline. This permits the use of harmonic imaging algorithms which use special amplification and filtering techniques to reduce the prevalence of artifacts. System 100 permits experimentation with unusual algorithms and displays such as multiple pulsed wave Doppler, tissue detection, carotid movement quantification, to be executed in conjunction with a standard B-mode image with velocity information.

Figure 14:
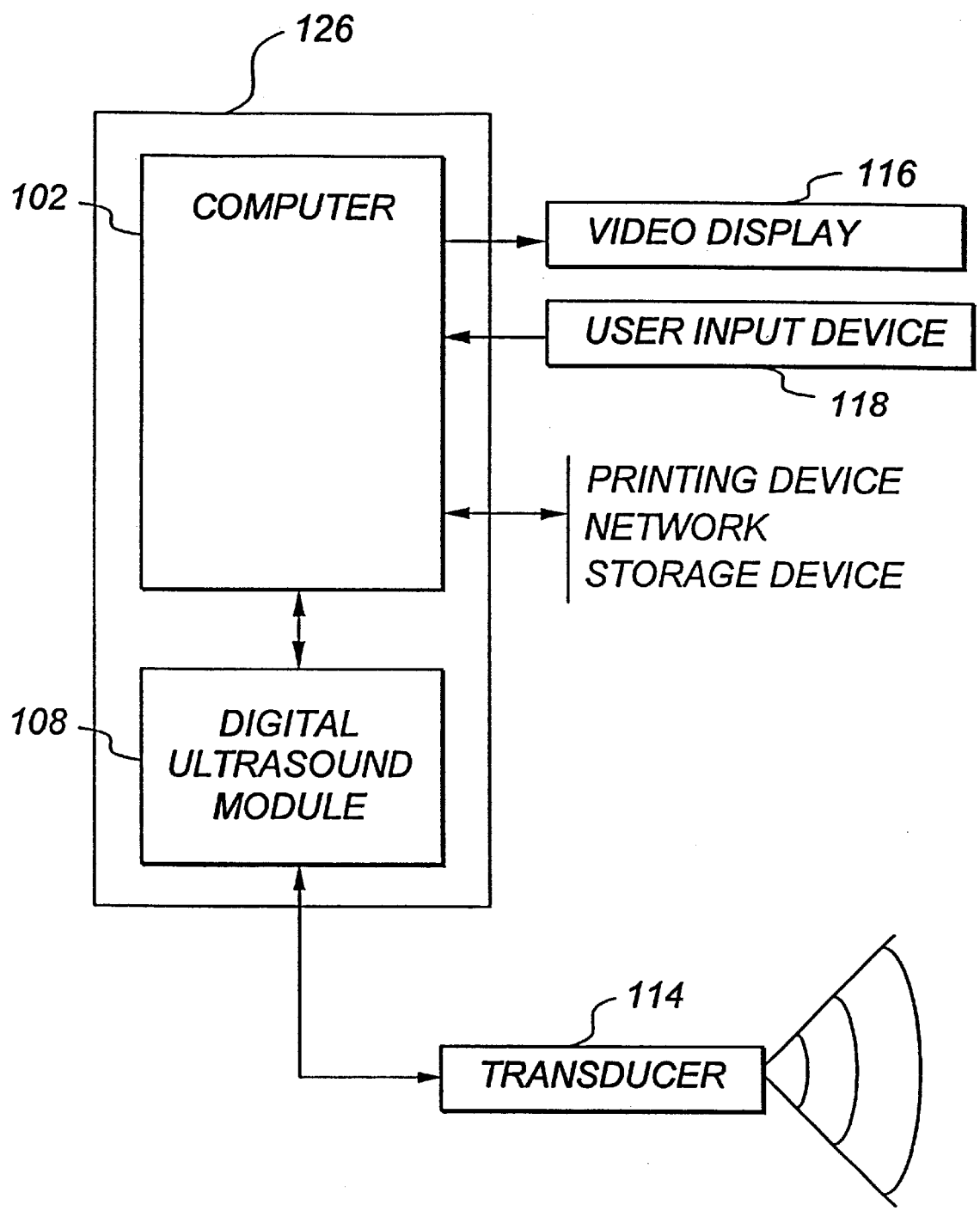

As will be apparent to those skilled in the art in the light of the foregoing disclosure, many alterations and modifications are possible in the practice of this invention without departing from the spirit or scope thereof. For example, module 108 and computer 102 may be housed in the same case. FIG. 14 is an ultrasound system for producing ultrasound images according to the second embodiment of the invention. In the second embodiment of the invention, the computer 102 and the ultrasound module 108 are enclosed in the same case 126. Case 126 may be a standard computer case, with enough space to contain all the components of the computer 102 and the ultrasound module 108. The second embodiment of the invention further has all the previously described capabilities of the first embodiment.

The scope of the invention is to be construed in accordance with the substance defined by the following claims.

What is claimed is:

1. A software configurable ultrasound imaging system comprising:

a. a computer adapted to run various programs for controlling the imaging system;

b. a signal pre-processing module operatively connected to the computer, said pre-processing module being adapted to be operatively coupled to an ultrasound transducer, said signal pre-processing module being configurable for different ultrasound operational modes for transducer driving signals and/or for processing echo signals into data vectors;

c. said computer being programmed for configuring said signal pre-processing module including providing configuration data and specified rayline parameters to said signal pre-processing module for each operational mode.

2. A software configurable ultrasound imaging system in accordance with claim 1 including a visual display operatively connected to said computer, and a display and scan conversion algorithm implemented in software running on said computer for displaying an ultrasound image in real time.

3. A software configurable ultrasound imaging system in accordance with claim 2 wherein the computer uses multi-tasking software to produce a real time display of an ultrasonic image.

4. A software configurable ultrasound imaging system in accordance with claim 1 wherein said signal pre-processing module includes a transmitting section, a receiving section and a pre-processing section, said transmitting section being configurable by the computer to provide different types of driving signals for the creation of different types of ultrasound wave forms;

said receiving section being configurable by the computer to beam-form the echo signal in different operational modes; and said pre-processing section being configurable by the computer to provide radio frequency (RF) ultrasound signal pre-processing in accordance with RF ultrasound signal pre-processing parameters supplied by the computer.

5. A software configurable ultrasound imaging system in accordance with claim 4 wherein said RF ultrasound signal pre-processing within said pre-processing section includes a RF calculator to convert the RF ultrasound signal into formatted data.

6. A software configurable ultrasound imaging system in accordance with claim 5 wherein said RF calculator operates in real time and outputs formatted data at a rate which is lower or equal to the RF ultrasound signal sampling rate.

7. A software configurable ultrasound imaging system in accordance with claim 6 wherein said pre-processing section of said signal pre-processing module includes a data signal pre-processor for further processing formatted data.

8. A software configurable ultrasound imaging system in accordance with claim 4 wherein the pre-processing section of said signal pre-processing module includes a data signal pre-processor.

9. A software configurable ultrasound imaging system in accordance with claim 4 wherein the computer is operatively connected to an interface for transmitting rayline parameters to the signal pre-processing module.

10. A software configurable ultrasound imaging system in accordance with claim 9 wherein rayline parameters are sequentially propagated and stored in the transmitting section, receiving section and pre-processing section of said signal pre-processing module.

11. A software configurable ultrasound imaging system in accordance with claim 4 wherein the computer includes an interface for storing and sequentially transmitting rayline parameters to the transmitting section, receiving section, and pre-processing section.

12. A software configurable ultrasound imaging system in accordance with claim 4 wherein each of said transmitting section, receiving section and pre-processing section includes a memory for storing data written into said memory by said computer.

13. A software configurable ultrasound imaging system in accordance with claim 4 wherein the receiving section includes a beam-former, said beam-former comprising a programmable summing circuit, programmable delay lines, and at least two programmable filters.

14. A software configurable ultrasound imaging system in accordance with claim 4 wherein the computer generates rayline parameters which are propagated to the signal pre-processing module for determining the manner in which transducer driving signals and echo signals are processed within a particular mode of operation, said rayline parameters including rayline transmitting parameters for the transmitting section, rayline receiving parameters for the receiving section, and rayline pre-processing parameters for the pre-processing section.

15. A software configurable ultrasound imaging system in accordance with claim 4 wherein the transmitting section, receiving section and pre-processing section of said signal pre-processing module include field programmable data array (FPGA) registers.

16. A software configurable ultrasound imaging system in accordance with claim 4 wherein the pre-processing section executes different pre-processing algorithms for different raylines and wherein said pre-processing algorithm is chosen according to said rayline parameters.

17. A software configurable ultrasound imaging system in accordance with claim 1 wherein said signal pre-processing module includes a pre-processing section, said pre-processing section including an echo level pre-processing unit for providing a detected echo level for a number of discrete points along a rayline and a digital signal pre-processing unit for calculating various data vector estimation functions of the ultrasound imaging system, said echo level pre-processing unit and said digital signal pre-processing unit being configurable by the computer for different modes of operation.

18. A software configurable ultrasound imaging system in accordance with claim 1 wherein the computer is a general purpose computer.

19. A software configurable ultrasound imaging system in accordance with claim 1 wherein the computer generates rayline parameters which are propagated to the signal pre-processing module for determining the manner in which transducer driving signals and echo signals are processed within a particular mode of operation.

* * * * *